(12) United States Patent
Han et al.

(10) Patent No.: US 8,772,472 B2
(45) Date of Patent: Jul. 8, 2014

(54) SIRNA CONJUGATE AND PREPARATION METHOD THEREOF

(75) Inventors: Bo Ram Han, Bucheon-si (KR); Han Oh Park, Daejeon (KR); Mi Sik Shin, Daejeon (KR); Sam Young Lee, Daejeon (KR)

(73) Assignee: Bioneer Corporation, Daejeon (KR)

( * ) Notice: Subject to any disclaimer, the term of this patent is extended or adjusted under 35 U.S.C. 154(b) by 0 days.

(21) Appl. No.: 13/613,071

(22) Filed: Sep. 13, 2012

(65) Prior Publication Data

US 2013/0096288 A1    Apr. 18, 2013

Related U.S. Application Data

(62) Division of application No. 13/319,885, filed as application No. PCT/KR2010/003039 on May 13, 2010.

(30) Foreign Application Priority Data

May 14, 2009    (KR) ........................ 10-2009-0042297

(51) Int. Cl.
*A61K 47/00*    (2006.01)
*A61K 9/107*    (2006.01)
*A61K 47/48*    (2006.01)
*A61K 47/34*    (2006.01)

(52) U.S. Cl.
CPC .............. *A61K 47/48* (2013.01); *A61K 9/1075* (2013.01); *A61K 47/48092* (2013.01); *A61K 47/48776* (2013.01); *A61K 47/34* (2013.01); *Y10S 977/773* (2013.01); *Y10S 977/906* (2013.01)
USPC ........................ 536/24.5; 977/773; 977/906

(58) Field of Classification Search
USPC ................................ 536/24.5; 977/773, 906
See application file for complete search history.

(56) References Cited

U.S. PATENT DOCUMENTS

| | | | |
|---|---|---|---|
| 6,221,959 B1 | 4/2001 | Kabanov et al. | |
| 2004/0249178 A1* | 12/2004 | Vargeese et al. | 552/506 |
| 2007/0072823 A1* | 3/2007 | Khvorova et al. | 514/44 |
| 2007/0135372 A1* | 6/2007 | MacLachlan et al. | 514/44 |
| 2011/0158906 A1* | 6/2011 | Mullen et al. | 424/1.73 |

FOREIGN PATENT DOCUMENTS

| | | | |
|---|---|---|---|
| KR | 1020070061770 A | | 6/2007 |
| WO | 2004087931 A1 | | 10/2004 |
| WO | 2007021142 A1 | | 2/2007 |

OTHER PUBLICATIONS

Kim et al., "PEG conjugated VEGF siRNA for anti-angiogenic gene therapy", Journal of Controlled Release, 2006, pp. 123-129, vol. 116.

Alshamsan et al., "Formulation and Delivery of siRNA by Oleic Acid and Stearic Acid Modified Polyethylenimine", Molecular Pharmaceutics, Dec. 2, 2008, pp. 121-133, vol. 6, No. 1.

Amarzguioui et al., "Tolerance for mutations and chemical modifications in a siRNA", Nucleic Acids Research, 2003, pp. 589-595, vol. 31, No. 2.

Ambrosini et al., "A novel anti-apoptosis gene, survivin, expressed in cancer and lymphoma", Nature Medicine, Aug. 1997, pp. 917-921, vol. 3, No. 8.

Braasch et al., "Biodistribution of phosphodiester and phosphorothioate siRNA", Bioorg. Med. Chem. Lett., 2004, pp. 1139-1143, vol. 14.

Chiu et al., "siRNA function in RNAi: A chemical modification analysis", RNA, 2003, pp. 1034-1048, vol. 9, No. 9.

Dawson et al., "Nanoparticles reconstruct lipids", Nature Nanotechnology, Feb. 2009, pp. 84-85, vol. 4.

Dejneka et al., "Ocular biodistribution of bevasiranib following a single intravitreal injection to rabbit eyes", Molecular Vision, 2008, pp. 997-1005, vol. 14.

Elbashir et al., "RNA interference is mediated by 21- and 22-nucleotide RNAs", Genes & Development, 2001, pp. 188-200, vol. 15.

Elbashir et al., "Functional anatomy of siRNAs for mediating efficiant RNAi in *Drosophila melanogaster* embryo lysate", The EMBO Journal, 2001, pp. 6877-6888, vol. 20, No. 23.

Elbashir et al., "Duplexes of 21-nucleotide RNAs mediate RNA interference in cultured mammalian cells", Nature, May 24, 2001, pp. 494-498, vol. 411.

Fire et al., "Potent and specific genetic interference by double-stranded RNA in *Caenorhabditis elegans*", Nature, Feb. 19, 1998, pp. 806-811, vol. 391.

Gary et al., "Polymer-based siRNA delivery: Perspectives on the fundamental and phenomenological distinictions from polymer-based DNA delivery", Journal of Controlled Release, 2007, pp. 64-73, vol. 121.

Kawakami et al., "Targeted Delivery Systems of Small Interfering RNA by Systemic Administration", Drug Metab. Pharmacokinet., 2007, pp. 142-151, vol. 22, No. 3.

Kim et al., "Comparative Evaluation of Target-Specific GFP Gene Silencing Efficiencies for Antisense ODN, Synthetic siRNA, and siRNA Plasmid Complexed with PEI-PEG-FOL Conjugate", Bioconjugate Chem., 2006, pp. 241-244, vol. 17, No. 1.

Lehrman, "Virus treatment questioned after gene therapy death", Nature, Oct. 7, 1999, pp. 517-518, vol. 401.

Million, "Therapeutic area crossroads: anti-angiogenesis", Nature Reviews, Feb. 2008, pp. 115-116, vol. 7.

(Continued)

*Primary Examiner* — Jennifer McDonald
(74) *Attorney, Agent, or Firm* — Hultquist, PLLC; Steven J. Hultquist; Mary B. Grant

(57) ABSTRACT

Provided are an siRNA-polymer conjugate, and a method for preparing the same, and more specifically, to a hybrid conjugate formed by covalently bonding siRNA and a polymeric compound for improving the in vivo stability of siRNA, and to a preparation method of the hybrid conjugate. The conjugate of the present invention can improve the in vivo stability of siRNA, thereby achieving an efficient delivery of therapeutic siRNA into cells and exhibiting the activity of siRNA even with a small dose of a relative low concentration. Therefore, the conjugate can advantageously be used as not only an siRNA treatment tool for cancers and other infectious disease, but also a novel type siRNA delivery system.

11 Claims, 17 Drawing Sheets

(56) References Cited

OTHER PUBLICATIONS

Novina et al., "The RNAi revolution", Nature, Jul. 8, 2004, pp. 161-164, vol. 430.

Rana, "Illuminating the silence: understanding the structure and function of small RNAs", Nature Reviews, Jan. 2007, pp. 23-36, vol. 8.

Sinha et al., "Polymer support oligonucleotide synthesis XVIII", Nucleic Acids Research, May 9, 1984, pp. 4539-4557, vol. 12, No. 11.

Soutschek et al., "Thereapeutic silencing of an endogenous gene by systemic administration of modified siRNAs", Nature, Nov. 11, 2004, pp. 173-178, vol. 432.

Tomari et al., "Perspective: machines for RNAi", Genes & Development, 2005, pp. 517-529, vol. 19.

Kim et al., "Systemic and Specific Delivery of Small Interfering RNAs to the Liver Mediated by Apolipoprotein A-I", Molecular Therapy, Jun. 2007, pp. 1145-1152, vol. 15, No. 6.

\* cited by examiner

FIG. 6
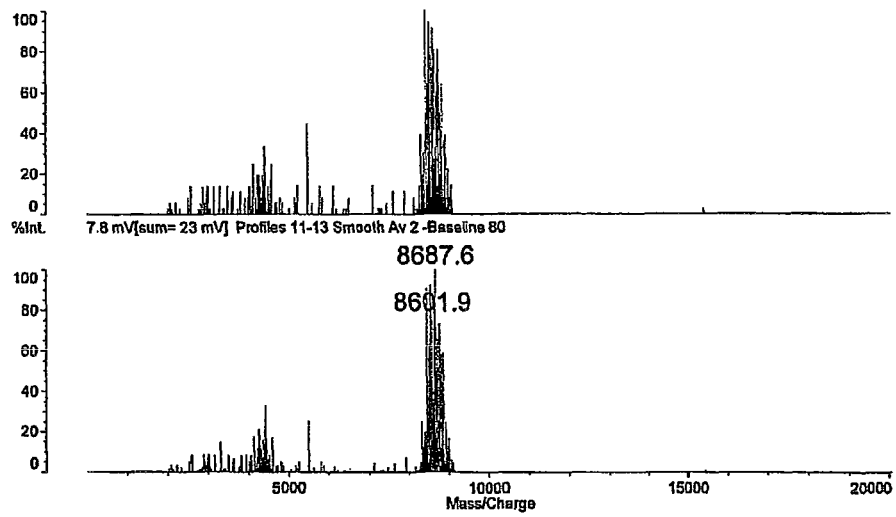
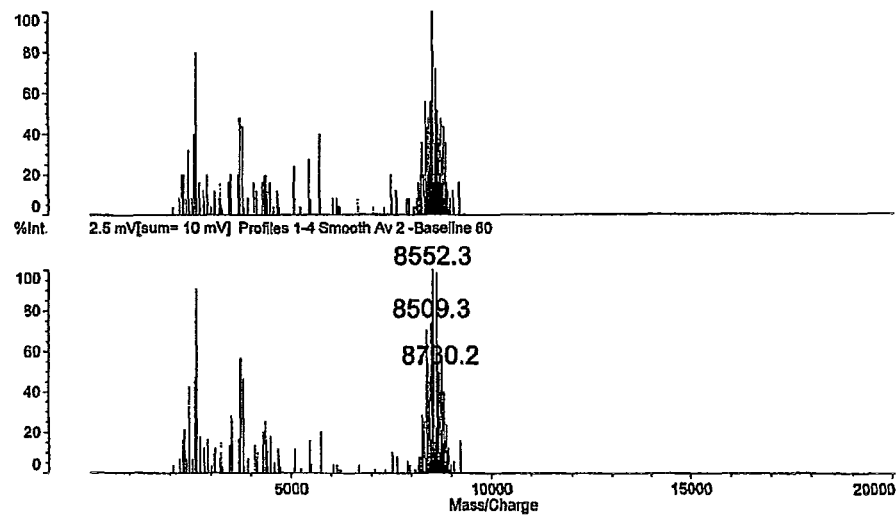

FIG. 7
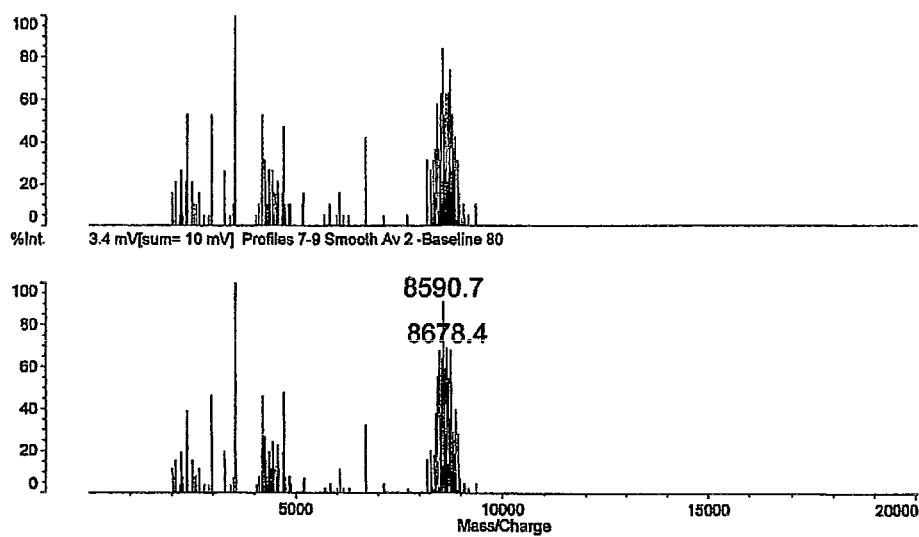
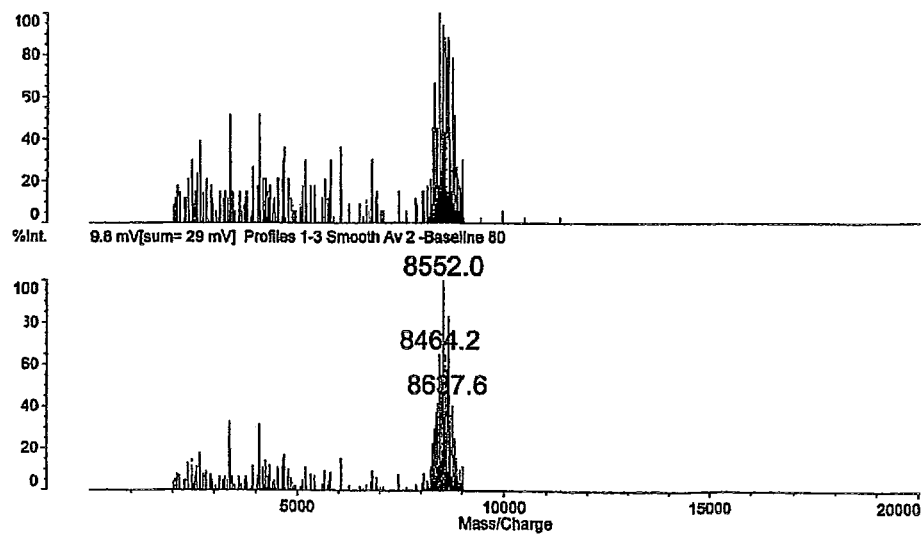

FIG. 8
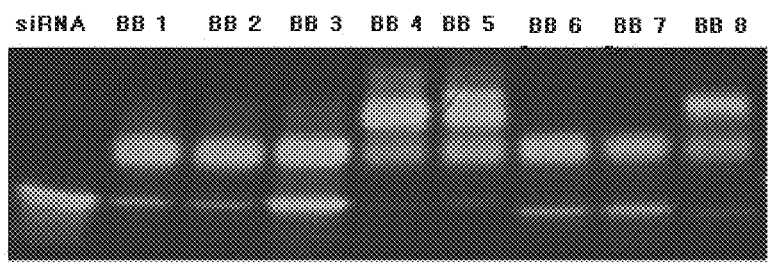
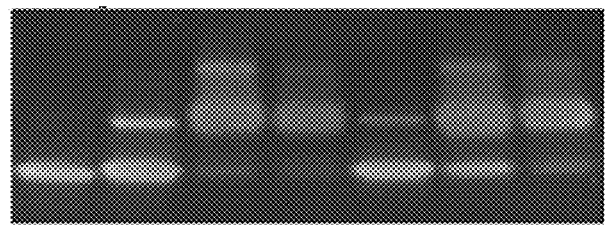
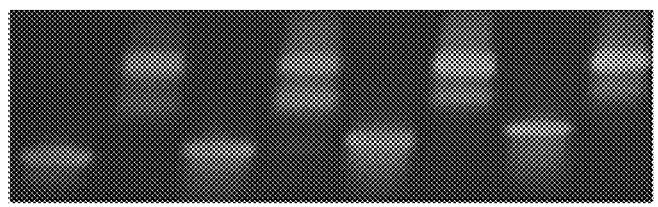
BB: conjugate

SEQUENCE LISTING

<160> NUMBER OF SEQ ID NOS: 5

<210> SEQ ID NO 1
<211> LENGTH: 19
<212> TYPE: RNA
<213> ORGANISM: Artificial Sequence
<220> FEATURE:
<223> OTHER INFORMATION: survivin siRNA sequence

<400> SEQUENCE: 1

```
aaggagauca acauuuuca                                                    19

<210> SEQ ID NO 2
<211> LENGTH: 23
<212> TYPE: RNA
<213> ORGANISM: Artificial Sequence
<220> FEATURE:
<223> OTHER INFORMATION: survivin si RNA sequence

<400> SEQUENCE: 2
aggaaaggag aucaacauuu uca                                               23

<210> SEQ ID NO 3
<211> LENGTH: 27
<212> TYPE: RNA
<213> ORGANISM: Artificial Sequence
<220> FEATURE:
<223> OTHER INFORMATION: survivin siRNA sequence

<400> SEQUENCE: 3
aggaaaggag aucaacauuu ucaaauu                                           27

<210> SEQ ID NO 4
<211> LENGTH: 31
<212> TYPE: RNA
<213> ORGANISM: Artificial Sequence
<220> FEATURE:
<223> OTHER INFORMATION: survivin siRNA sequence

<400> SEQUENCE: 4
aaaggagauc aacauuuuca aauuagaugu u                                      31

<210> SEQ ID NO 5
<211> LENGTH: 19
<212> TYPE: RNA
<213> ORGANISM: Artificial Sequence
<220> FEATURE:
<223> OTHER INFORMATION: antisense to SEQ ID NO. 1

<400> SEQUENCE: 5
ugaaaauguu gaucccuu                                                     19
```

SIRNA CONJUGATE AND PREPARATION METHOD THEREOF

CROSS REFERENCE TO RELATED APPLICATIONS

This application is a divisional application of co-pending U.S. patent application Ser. No. 13/319,885, filed Jan. 23, 2012, which is the United States national stage filing under 35 U.S.C. §371 of International Application No. PCT/KR2010/003039, filed May 13, 2010, and which claims priority to Korean Patent Application No. KR 10-2009-0042297, filed May 14, 2009, all of which are incorporated by reference herein in their entirety.

The Sequence Listing associated with this application is filed in electronic format via EFS-Web and is hereby incorporated by reference into the specification in its entirety. The name of the text file containing the Sequence Listing is 122379_ST25.txt. The size of the text file is 1,364 bytes, and the text file was created on Aug. 15, 2012

TECHNICAL FIELD

The present invention relates to a conjugate in which a polymer compound for improving delivery of siRNA useful in gene therapy of cancers and other infectious diseases is conjugated to the siRNA by using a degradable or a non-degradable bond, a method for preparing the conjugate, and a method for delivering the siRNA using the conjugate.

BACKGROUND ART

RNA interference refers to a mechanism, which is post-transcriptional gene silencing initiated by a double-stranded RNA (dsRNA) via nucleotide sequence specific manner in a gene expression process, and this mechanism is first found in *C. elegans*, and commonly found in plant, fruitfly, and vertebrate (Fire et al., Nature, 391:806-811, 1998; Novina & Sharp, Nature, 430:161-164, 2004). It has been known that RNA interference occurs in such a manner that dsRNA of 19~25 bp entering in the cell is bound with an RISC(RNA-induced silencing complex), and only an antisense (guide) strand is bound with mRNA such that it is complementary to the nucleotide sequence of the mRNA, thereby degrading target mRNA by endonuclease domains existing in the RICS (Rana, T. M., Nat. Rev. Mol. Cell Biol., 8:23-36, 2007; Tomari, Y. and Zamore, P. D., Genes Dev., 19: 517-529, 2005).

When the dsRNA is delivered into a cell, it is specifically bound to a target mRNA sequence to degrade the mRNA, and thereby, it is considered as a new tool capable of regulating gene expression. However, in case of human, it was difficult to obtain RNAi effect due to the induction of an antiviral interferon pathway on introduction of dsRNA into human cells. In 2001, Elbashir and Tuschl et al., found that the introduction of small dsRNA of 21 nt length (nucleotides length) into human cells did not cause the interferon pathway but specifically degraded the target mRNA (Elbashir, S. M., Harborth, J., Lendeckel, W., Yalcin, A., Weber, K., Tuschl, T., Nature, 411, 494-498, 2001; Elbashir, S. M., Lendeckel, W., Tuschl, T., Genes & Dev., 15, 188-200, 2001; Elbashir, S. M., Martinez, J., Patkaniowska, A., Lendeckel, W., Tuschl, T., EMBO J., 20, 6877-6888, 2001). Thereafter, dsRNA of 21 nt length has been spotlighted as a tool of new functional genomics and named as small interfering RNA (siRNA).

The siRNA is a substance gaining a lot of interest as a agent for gene therapy ever since it was reported to have an excellent effect in inhibiting expression of a specific gene in animal cells. In effect, because of its high activity and precise gene selectivity, siRNA is expected to be an alternative therapeutic agent to an antisense oligonuceotide (ODN) currently being used as a therapeutic agent, as a result of a 20-year research (Dana J. Gary et al. Journal of Controlled Release 121:64-73, 2007). A siRNA technique aiming to therapy has great advantages in that it is easily designed compared with other medicines and has high target selectivity and a property of inhibiting expression of a specific gene. In addition, it is less toxic because RNA interference suppresses gene expression by using a mechanism naturally existing in a living system. 'Bevasiranib', recently developed as a therapeutic agent for wet age-related macular disease by OPKO Inc., is a siRNA which acts selectively on a vascular endothelial growth factor (VEGF) inducing neovascularization to inhibit expression of the VEGF, and passes through three phases of clinical trial (Dejneka N S et al., Mol. Vis., 28(14):997-1005, 2008). Besides, therapeutic agents including siRNAs targeting various genes are currently being developed (Ryan P. Million, Nature Reviews Drug Discovery 7: 115-116, 2008).

Despite various results showing that specific expression inhibition is induced in vivo through RNA interference, in vivo siRNA delivery has many problems to be solved, such as degradation by enzymes in the blood, interaction with components in the blood, and non-specific delivery to cells (Shigeru Kawakami and Mitsuru Hashida, Drug Metab. Pharmacokinet. 22(3): 142-151, 2007). Attempts to overcome these problems are in progress by partially using nuclease resistant nucleoside analogues or improving delivery techniques.

Examples of the improved delivery techniques include gene delivery techniques using viruses such as adenoviruses, retroviruses, etc., and gene delivery techniques by non-viral vectors using liposomes, cationic lipid, and cationic polymer compounds. However, viral carriers has a problem in safety since delivered genes are likely to be integrated into a chromosome of a host to induce abnormality in normal functions of genes of the host and activate oncogenes, and in addition, may cause autoimmune diseases due to successive expression of viral genes even in small amounts, or may not lead to efficient protective immunity in a case where modified viral infection is induced from the viral carriers. Meanwhile, non-viral carriers are less efficient than the viral carriers, but have advantages of low side effects and inexpensive production costs, considering in vivo safety and economic feasibility (Lehrman S., Nature. 401(6753): 517-518, 1999). In addition, non-viral delivery methods require to effectively protect enzymatic or non-enzymatic degradation in order to deliver RNA molecules including siRNA, one method of which is to utilize DNA expression plasmids encoding a short hairpin RNA (shRNA). A system through DNA has an advantage in that siRNA is expressed only while an expression vector exists. Moreover, a recent study on chemical modification of siRNA has proposed a method for improving the stability against nucleases and the low intracellular uptake (Shigery Kawakami and Mitsuru Hashida. Drug Metab. Parmacokinet. 22(3): 142-151, 2007).

In one type of chemical modification of siRNA, a phosphorodiester bond, which is a part degraded by the nuclease, was modified with a phosphorothioate linkage or the 2' portion of a pentose is modified with 2'-O-meRNA, 2'-deoxy-2'-fluouridine, or a locked nucleic acid (LNA) formed by linking the 2' portion and the 4' portion, and as a result, the stability in the serum was improved ((Braasch D. A. et al. Bioorg. Med. Chem. Lett. 14:1139-1143, 2003; Chiu Y. L. and Rana T. M., RNA, 9:1034-1048, 2003; Amarzguioui M. et al. Nucleic Acid Res. 31:589-595, 2003). In another type of chemical modification, a functional group is linked to a 3'-end region of a sense (anti-guide) strand, resulting in improvement in pharmacokinetic characteristics compared with a control, and high efficiency is induced at the time of application in vivo through a balance between hydrophilicity and hydrophobilicity of siRNA (Soutschek J. et al. Nature 432:173-178 2004).

However, the above methods still leave much to be desired in order to protect siRNA from nucleases and improve the efficiency of cell-membrane permeability.

For that reason, the inventors have found that a conjugate, in which hydrophilic or hydrophobic polymer compound is conjugated to siRNA by using a degradable or a non-degradable bond, improved in vivo stability of siRNA, and, based on this, has completed the present invention.

DISCLOSURE

Technical Problem

An object of the present invention is to provide a conjugate in which a hydrophilic or hydrophobic polymer compound, which is a biocompatible polymer compound, is conjugated to an end of a sense strand or an antisense strand of siRNA by using a degradable or non-degradable bond, in order to improve the intracellular delivery efficiency of the siRNA.

Another object of the present invention is to provide a solid support containing a polymer compound, especially, a polymer compound of which stability is proved when applied to human body, for example, polyethylene glycol (PEG), and a method for efficiently preparing an oligonucleotide including RNA, DNA, RNA-DNA chimera, and analog thereof, in which PEG is bound to the 3' end thereof by using the support.

Still another object of the present invention is to provide a method for preparing the siRNA conjugate and a method for delivering siRNA using the siRNA conjugate.

Technical Solution

In order to achieve the above objects, a first of the present invention provides an siRNA-polymer compound conjugate of the following structure:

A-X—R—Y—B (wherein, A and B are independently a hydrophilic polymer or hydrophobic polymer compound; X and Y are independently a simple covalent bond or a linker-mediated covalent bond; and R is siRNA).

A second of the present invention provides an siRNA-polymer compound conjugate of the following structure:

A-X—R (wherein, A is a hydrophobic polymer compound; X is a simple covalent bond or a linker-mediated covalent bond; and R is siRNA).

A third of the present invention provides a conjugate in which a single strand of the siRNA (R) is composed of 19 to 31 nucleotides.

A fourth of the present invention provides a conjugate in which the hydrophobic polymer compound (A) has a molecular weight of 250 to 1,000.

A fifth of the present invention provides a conjugate in which the hydrophobic polymer compound (A) is $C_{16}$~$C_{50}$ hydrocarbon or cholesterol.

A sixth of the present invention provides a conjugate in which the covalent bond (X, Y) is a non-degradable bond or a degradable bond.

A seventh of the present invention provides a conjugate in which the non-degradable bond is an amide bond or a phosphate bond.

An eighth of the present invention provides a conjugate in which the degradable bond is selected from a disulfide bond, an acid-cleavable bond, an ester bond, an anhydride bond, a biodegradable bond and an enzyme-cleavable bond.

A ninth of the present invention provides a conjugate in which the hydrophilic polymer compound (A or B) is a non-ionic polymer compound having a molecular weight of 1,000 to 10,000.

A tenth of the present invention provides a conjugate in which the hydrophilic polymer compound is selected from a group consisting of polyethylene glycol (PEG), polyvinylpyrolidone, and polyoxazoline.

An eleventh of the present invention provides a polyethylene glycol-bound solid support of the following structure:

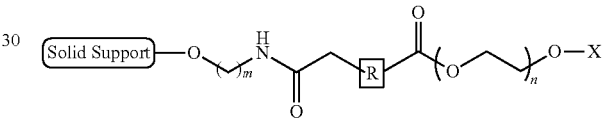

[where, R is alkyl, alkenyl, alkynyl, aryl, arylalkyl, heteroalkyl, or heteroaryl; m is an integer of 2 to 18; n is an integer of 5 to 120; and X is hydrogen, 4-monomethoxytrityl, 4,4'-dimethoxytrityl, or 4,4',4''-trimethoxytrityl].

A twelfth of the present invention provides a polyethylene glycol-bound solid support in which the solid support is controlled pore glass (CPG).

A thirteenth of the present invention provides a polyethylene glycol-bound solid support in which the CPG has a diameter of 40~180 μm and a pore size of 500 Å~3000 Å.

A fourteenth of the present invention provides a polyethylene glycol-bound solid support which is 3'-PEG-CPG having the following structural formula IV:

[Structural Formula IV]

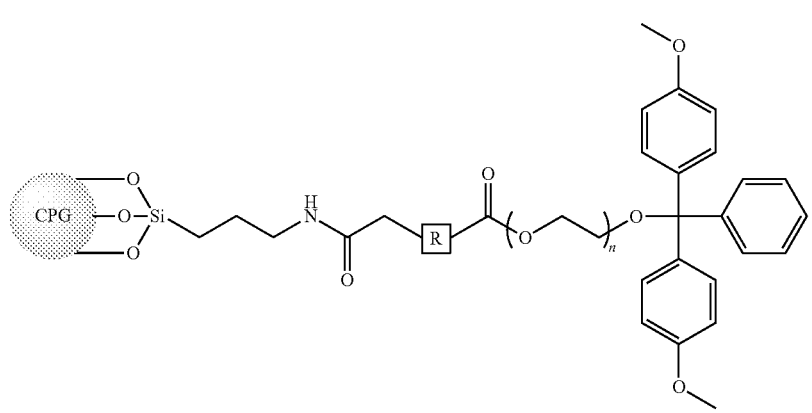

A fifteenth of the present invention provides a method for preparing 3'-PEG-CPG the method including:

1) reacting CPG with 3-aminopropyltriethoxysilane to form long chain alkyl amine controlled pore glass (LCAA-CPG);

2) reacting polyethylene glycol with 4,4'-dimethoxytrityl chloride to form 2-[bis-(4-dimethoxytrityl)-poly(ethylene glycol)];

3) reacting the compound formed in the step 2) and a compound of the following chemical formula I to form a compound of the following structural formula I;

4) reacting the formed compound of the following structural formula I and 4-nitrophenylchloroformate to form a compound of the following structural formula II;

5) reacting the compound of the following structural formula I formed in the step 3) and N-succinimidyl trifluoroacetic acid to form a compound of the following structural formula III; and 6) reacting the LCAA-CPG compound formed in the step 1) with the compounds of the following structural formulas I, II, and III respectively formed in the steps 3) to 5), respectively.

[chemical Formula 1]

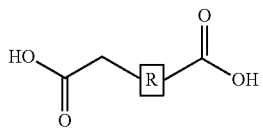

[Structural Formula I]

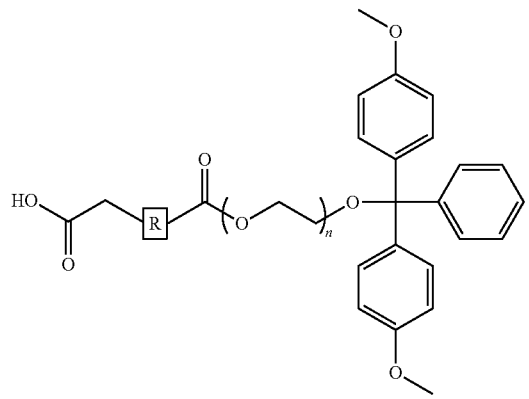

[Structural Formula II]

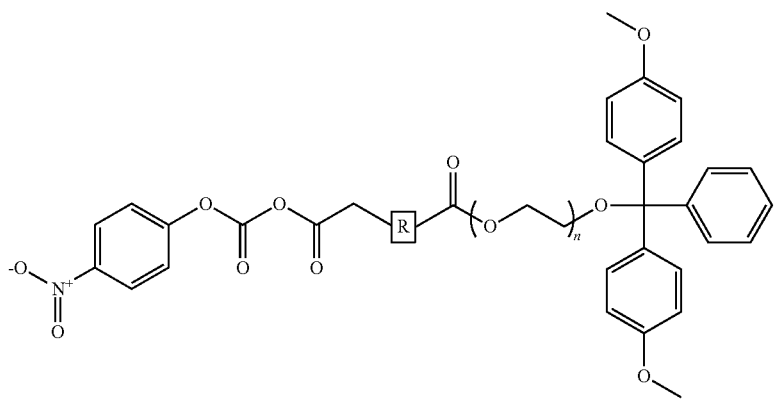

[Structural Formula III]

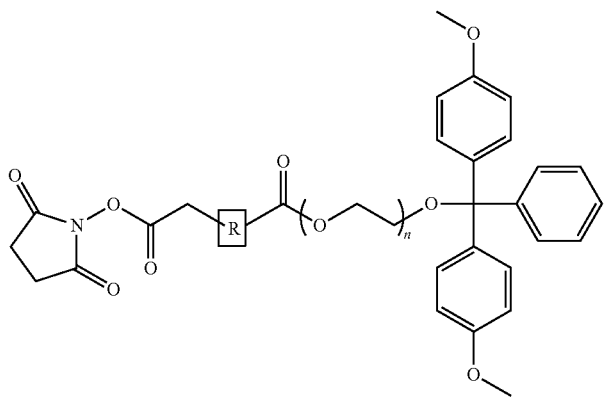

-continued

[Structural Formula IV]

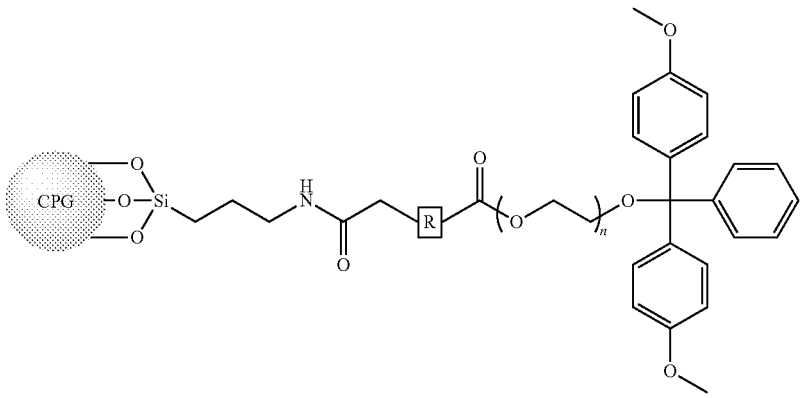

[where, R is alkyl, alkenyl, alkynyl, aryl, arylalkyl, heteroalkyl, or heteroaryl; and n is an integer of no less than 5 and no more than 120].

A sixteenth of the present invention provides a method for preparing an siRNA conjugate, the method including:
1) preparing an siRNA for a target gene by using the polyethylene glycol-bound solid support of the eleventh of the present invention; and
2) linking an end group of the siRNA and polyethylene glycol by a covalent bond.

A seventeenth of the present invention provides a nanoparticle consisting of siRNA conjugates of the first or second of the present invention.

An eighteenth of the present invention provides a method for gene therapy, including:
1) preparing the nanoparticles of the seventeenth of the present invention; and
2) administering the nanoparticles into the body of an animal.

A nineteenth of the present invention provides a method for gene therapy in which the nanoparticles are administered into the body by oral administration or intravenous injection.

A twentieth of the present invention provides a pharmaceutical composition including a pharmaceutically effective amount of the siRNA conjugates of the first or second of the present invention.

A twenty-first of the present invention provides a pharmaceutical composition including a pharmaceutically effective amount of the nanoparticles of the seventeenth of the present invention.

Hereinafter, the present invention will be described in detail.

The present invention provides an siRNA-polymer compound conjugate of the following structure:

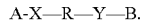

Wherein, A and B are independently a hydrophilic polymer or hydrophobic polymer compound; X and Y are independently a simple covalent bond or a linker-mediated covalent bond; and R is siRNA.

Moreover, the present invention provides an siRNA-polymer compound conjugate of the following structure:

Wherein, A is a hydrophobic polymer compound; X is a simple covalent bond or a linker-mediated covalent bond; and R is siRNA.

In the conjugate of the present invention, an oligonucleotide strand of the siRNA may include 19 to 31 nucleotides. Any siRNA derived from genes that is used or is likely to be used for gene therapy or study may be employed as the siRNA usable in the present invention.

The hydrophobic polymer compound may be a hydrophobic polymer compound having a molecular weight of 250 to 1,000. Examples of the hydrophobic polymer compound may include hydrocarbon, preferably, C16~C50 hydrocarbon, and cholesterol. Here, the hydrophobic polymer compound is not limited to only the hydrocarbon and the cholesterol.

The hydrophobic polymer compound causes a hydrophobic interaction to function to form a micelle consisting of siRNA-hydrophobic polymer compound conjugates. Among the hydrophobic polymer compounds, especially, the saturated hydrocarbon has an advantage in that it can be easily conjugated to the siRNA during manufacturing of the siRNA, and thus, it is very suitable for manufacturing conjugates of the present invention.

Also, the covalent bond (i.e., X, Y) may be any one of a non-degradable or a degradable bond. Here, there may be an amide bond or a phosphate bond in the non-degradable bond, and there may be a disulfide bond, an acid-cleavable bond, an ester bond, an anhydride bond, a biodegradable bond and an enzyme-cleavable bond in the degradable bond. However, the non-degradable or the degradable bond is not limited thereto.

The linker mediating the bond covalently binds the hydrophilic polymer (or the hydrophobic polymer) and an end of a residue derived from the siRNA, and is not particularly limited as long as it can provide a degradable bond in a certain environment, as necessary. Therefore, the linker may include any compound that can be bound with the siRNA and/or the hydrophilic polymer (or the hydrophobic polymer) to activate them during the manufacturing procedure of the conjugate.

Also, the hydrophilic polymer compound may be a non-ionic polymer compound having a molecular weight of 1,000 to 10,000. For example, the hydrophilic polymer compound may include a non-ionic hydrophilic polymer compound of polyethylene glycol, polyvinylpyrolidone, polyoxazoline, and the like, but is not limited thereto.

A functional group of the hydrophilic polymer compound may be replaced by another functional group, as necessary. Among the hydrophilic polymer compounds, particularly, PEG is very suitable for manufacturing the conjugates of the present invention since it has various molecular weights, has an end capable of introducing functional groups, has excellent biocompatibility, does not induce immune reactions, and increases the water-solubility to improve gene delivery efficiency in vivo.

Moreover, the present invention provides a polyethylene glycol-bound solid support of the following structure:

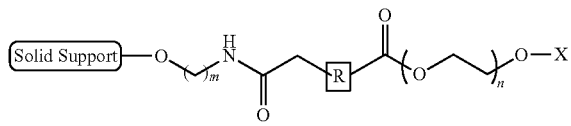

Wherein, the solid support includes, for example, CPG, polystyrene, silica gel, cellulose paper, etc., but is not necessarily limited thereto; R is alkyl, alkenyl, alkynyl, aryl, arylalkyl, heteroalkyl, or heteroaryl; m is an integer of 2 to 18; n is an integer of 5 to 120 (molar mass 282~5300); and X is 4-monomethoxytrityl, 4,4'-dimethoxytrityl, or 4,4',4"-trimethoxytrityl] and removed after acid treatment to become hydrogen. In a case where the solid support is CPG, it may have a diameter of 40~180 μm and a pore size of 500 Å~3000 Å.

Also, the present invention provides a polyethylene glycol-bound solid support in which 3'-PEG-CPG having the following structural formula IV is bound:

[Structural Formula IV]

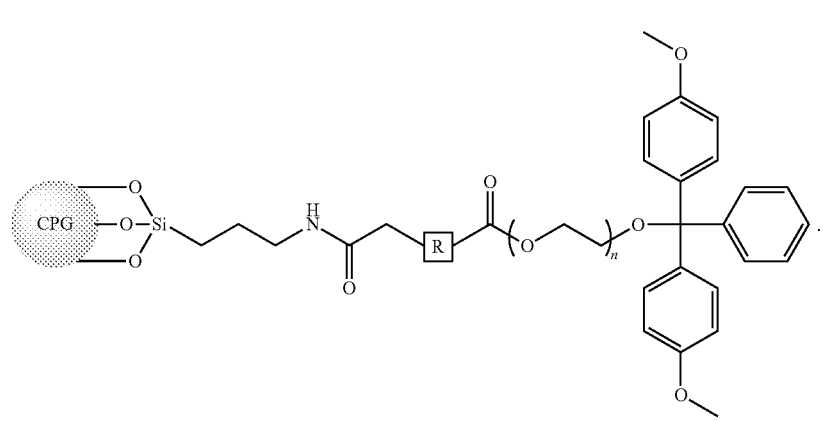

Moreover, the present invention provides a method for preparing 3'-PEG-CPG of the following structural formula IV, the method including:

1) reacting CPG with 3-aminopropyltriethoxysilane to form LCAA-CPG;

2) reacting polyethylene glycol with 4,4'-dimethoxytrityl chloride to form 2-[bis-(4-dimethoxytrityl)-poly(ethylene glycol)];

3) reacting the compound formed in the step 2) and a compound of the following formula I to form a compound of the following structural formula I;

4) reacting the formed compound of the following structural formula I and 4-nitrophenylchloroformate to form a compound of the following structural formula II;

5) reacting the compound of the following structural formula I formed in the step 3) and N-succinimidyl trifluoroacetic acid to form a compound of the following structural formula III; and 6) reacting the LCAA-CPG compound formed in the step 1) with the compounds of the following structural formulas I, II, and III respectively formed in the steps 3) to 5), respectively.

[Formula 1]
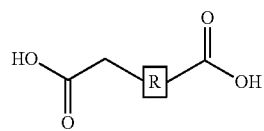
[Structural Formula I]
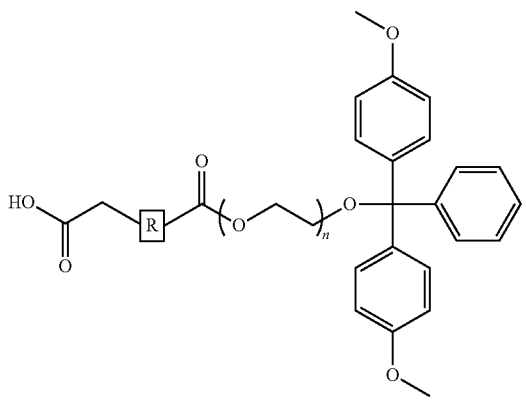
[Structural Formula II]
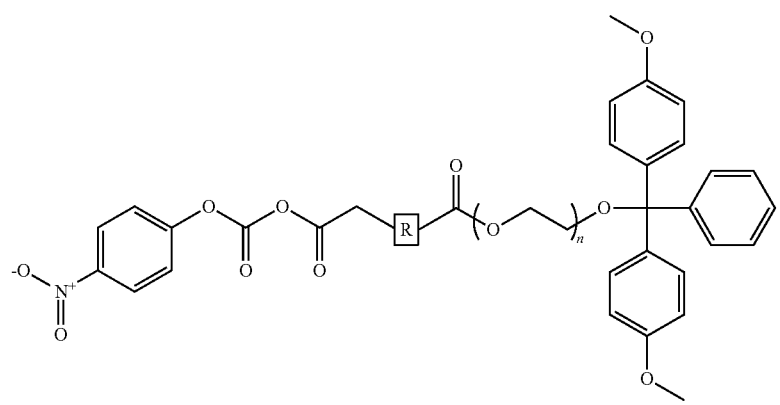
[Structural Formula III]
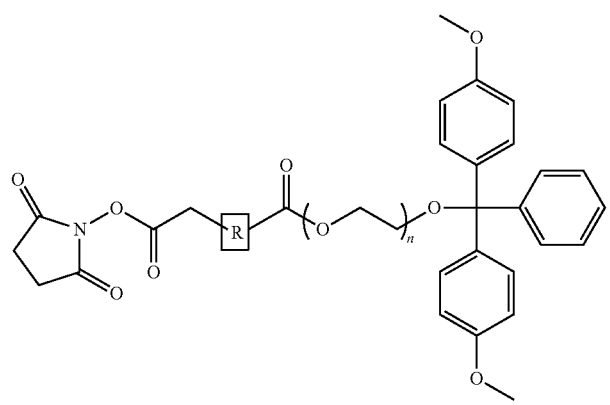
[Structural Formula IV]
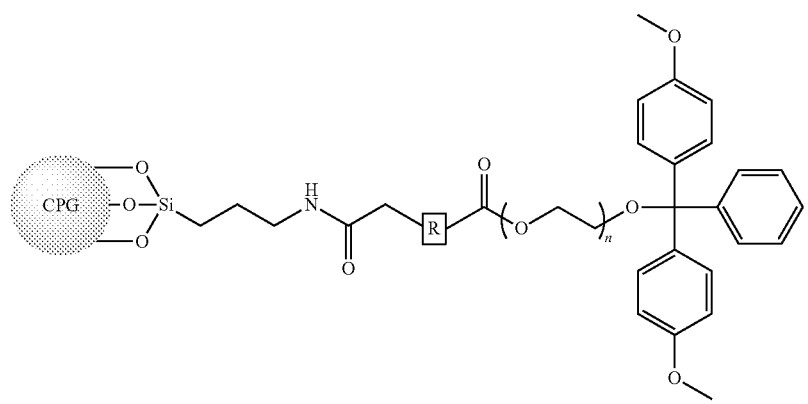

[where, R is alkyl, alkenyl, alkynyl, aryl, arylalkyl, heteroalkyl, or heteroaryl; and n is an integer of no less than 5 and no more than 120].

Also, the present invention provides a method for preparing an conjugate comprising siRNA and PEG by using the polyethylene glycol-bound solid support. More specifically, a method for preparing an siRNA conjugate is provided, the method including:

1) preparing an siRNA for a target gene by using the polyethylene glycol-bound solid support; and 2) linking an end group of the siRNA and polyethylene glycol by a covalent bond. Through this, oligonucleotides including RNA, DNA, RNA-DNA chimera, and analog thereof can be efficiently prepared.

According to a preferred embodiment of the present invention, the siRNA can be prepared by linking phosphordiester bonds building an RNA backbone structure, using β-cyanoethyl phosphoramidite (Shina et al. Nucleic Acids Research, 12:4539-4557, 1984). For example, a series of procedures consisting of deblocking, coupling, oxidation and capping were repeatedly performed on a sold support on which nucleotide was attached, by using an RNA synthesizer, to obtain the reactant containing a desired length of RNA. However, the present invention is not limited thereto.

Also, the present invention provides a nanoparticle consisting of siRNA conjugates.

The siRNA-polymer compound conjugates of the present invention can form a nanoparticle structure by interaction therebetween, and the siRNA-polymer compound conjugate and the nanoparticle consisting of the siRNA-polymer compound conjugates thus obtained improve intracellular delivery of siRNA and can be applicable for therapeutic treatment of disease models. The preparation of conjugates, and characteristics and intracellular delivery efficiency and effect of the nanoparticle consisting of the conjugates will be in detail described in the examples to be described later.

Also, the present invention provides a method for gene therapy using the nanoparticle.

More specifically, the method for gene therapy includes preparing the nanoparticles each consisting of the siRNA-polymer compound conjugates and administering the nanoparticles into the body of an animal.

Also, the present invention provides a pharmaceutical composition including a pharmaceutically effective amount of the nanoparticles each consisting of the siRNA conjugates.

The composition of the present invention can be prepared to include one or more of pharmaceutically acceptable carriers in addition to the above-described active components, for administration. The pharmaceutically acceptable carrier needs to be compatible with the active components of the present invention. The pharmaceutically acceptable carrier may be used by mixing with saline solution, sterilized water, Ringer's solution, buffered saline solution, dextrose solution, maltodextrin solution, glycerol and ethanol, and one or more thereof, and as necessary, other common additives such as antioxidants, buffer solution, bacteriostatic agents, or the like, may be added thereto. In addition, diluents, dispersants, surfactants, binders, and lubricants can be adjunctively added thereto to formulate formulations for injection such as aqueous solution, suspension, emulsion, or the like. Furthermore, the composition of the present invention can be preferably formulated according to specific diseases or components, by using appropriate methods in the art or methods disclosed in Remington's pharmaceutical Science (Mack Publishing company, Easton Pa.).

The pharmaceutical composition of the present invention can be determined by those skilled in the art, based on syndromes and disease severity of patients. Also, the pharmaceutical composition of the present invention can be formulated in various types such as powder, tablet, capsule, liquid, injectable, ointment, syrup, and the like, and can be provided in single-dosage or multi-dosage container, for example, a sealed ample, a bottle, or the like.

The pharmaceutical composition of the present invention can be orally or parenterally administered. The administration route of the pharmaceutical composition according to the present invention may include, but is not limited to, oral, intravenous, intramuscular, intramedullary, intrathecal, intracardiac, dermal, subcutaneous, intraperitoneal, enteral, sublingual, or topical administration.

For this clinical administration, the pharmaceutical composition of the present invention can be formulated in an appropriate formulation by using the known arts. The dosage of the composition of the present invention has various ranges depending on weight, age, gender, health status, diet, administration time and method, excretion rate, and disease severity of patient, and can be easily determined by those skilled in the art.

Advantageous Effects

The nanoparticle consisting of siRNA-polymer compound conjugates of the present invention can improve in vivo stability of siRNA to efficiently deliver a therapeutic siRNA into the cell, and can be very useful in a basic research for biotechnology and medical industry as a new type of siRNA delivery system, as well as a tool for siRNA treatment of cancers and other infective diseases since it can exhibit siRNA activity in a relatively low concentration of dosage even without transfection reagents.

DESCRIPTION OF DRAWINGS

FIG. 6 shows Maldi-T of molecular weight data after manufacturing of 3'-PEG-CPG and an oligonucleotide (siRNA) in Example 1-3;

FIG. 7 shows Maldi-T of molecular weight data after manufacturing of 3'-PEG-CPG and an oligonucleotide (siRNA) in Example 1-4;

FIG. 8 shows an electrophoresis photograph of a naked siRNA in which none of polymer compounds are conjugated, and siRNA-polymer compound conjugates in which a hydrophilic or hydrophobic polymer compound is conjugated (The siRNA means naked siRNA and respective conjugates represent siRNA-polymer compound conjugates shown in Table 1. Also, 19mer, 23mer, 27mer, and 31mer mean siRNAs consisting of 19, 23, 27, and 31 nucleotides, respectively, and they all were used to prepare siRNA-polymer compound conjugates in a structure of the siRNA conjugate 4);

BEST MODE

Hereinafter, the exemplary embodiments of the present invention will be described in detail. However, the following exemplary embodiments describe the present invention by way of example only but are not limited thereto.

Example 1

Preparation of Solid Support for Preparing 3'-PEG Oligonucleotide

Example 1-1

Preparation of 3'-PEG Reagents (Compounds A, B, and C) for Binding with LCAA-CPG In the subsequent example, 3'-PEG-CPG was prepared as shown in the following reaction formula.

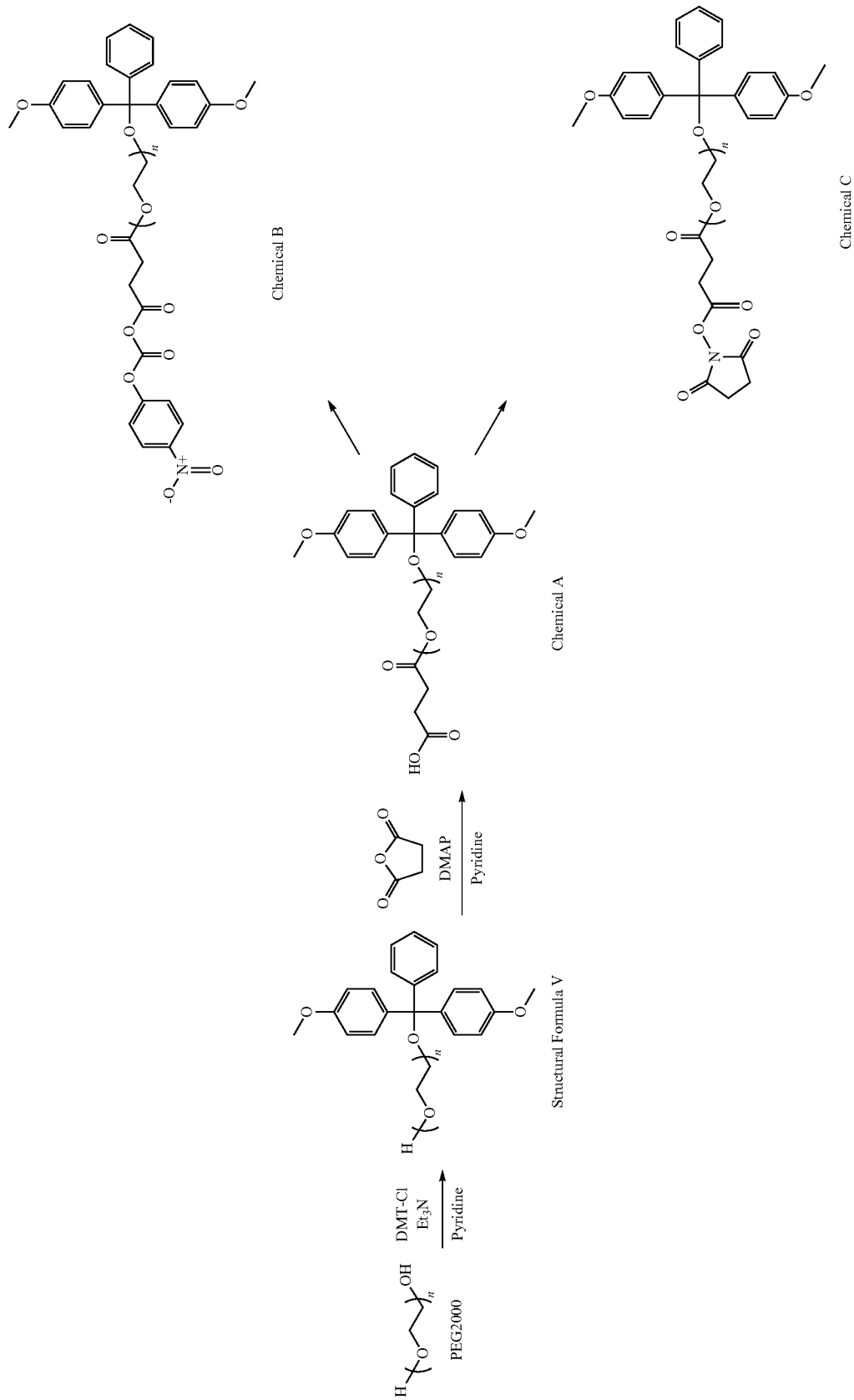

Example 1-1-1

Preparation of 2-[bis-(4-dimethoxytrityl)-poly(ethylene glycol)]

30 g (15 mmol) of polyethylene glycol 2000 (Alfa Aesar GmbH & Co. KG, Germany), as a starting material, was dissolved in 270 ml of pyridine (Sigma Aldrich, USA), followed by addition of 3.55 ml (25.5 mmol) of triethylamine (Sigma Aldrich, USA) and 7.12 g (21 mmol) of 4,4'-dimethoxy trityl chloride (GL biochem, China), and then the resultant substance was reacted at room temperature for 20 hours. The reactant mixture after completion of reaction was concentrated, and extracted with 450 ml of ethyl acetate and 450 ml of water, followed by vacuum evaporation and then vacuum drying, to obtain 2-[bis-(4-dimethoxytrityl)-poly(ethylene glycol) 23 g (66%).

Figure 1:
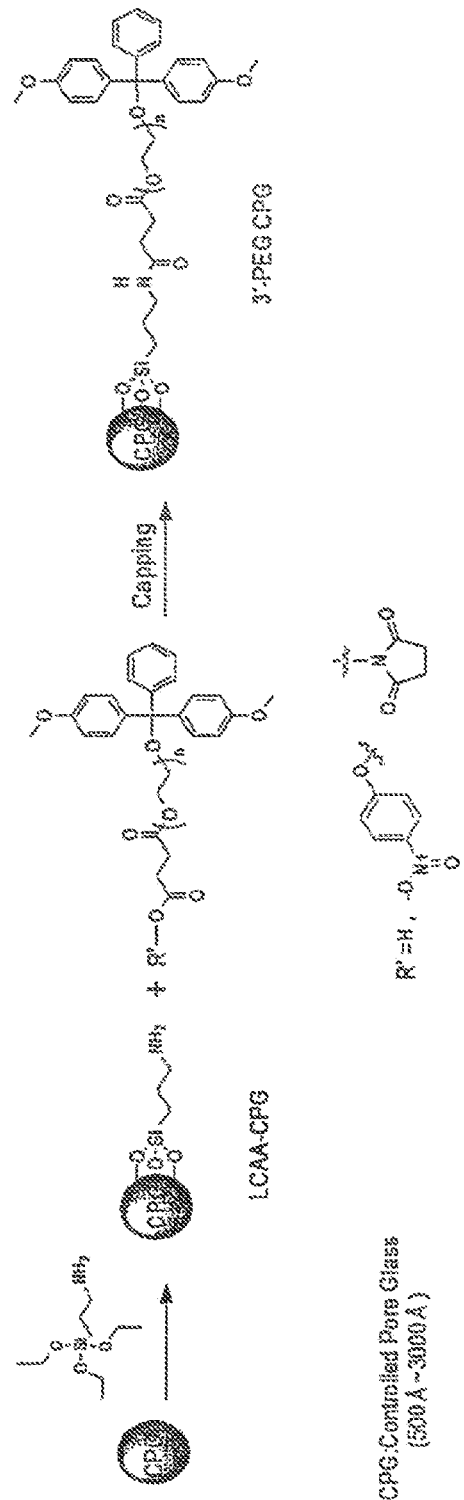
FIG. 1 shows a structural formula of 3'-PEG-CPG prepared.
Figure 2:
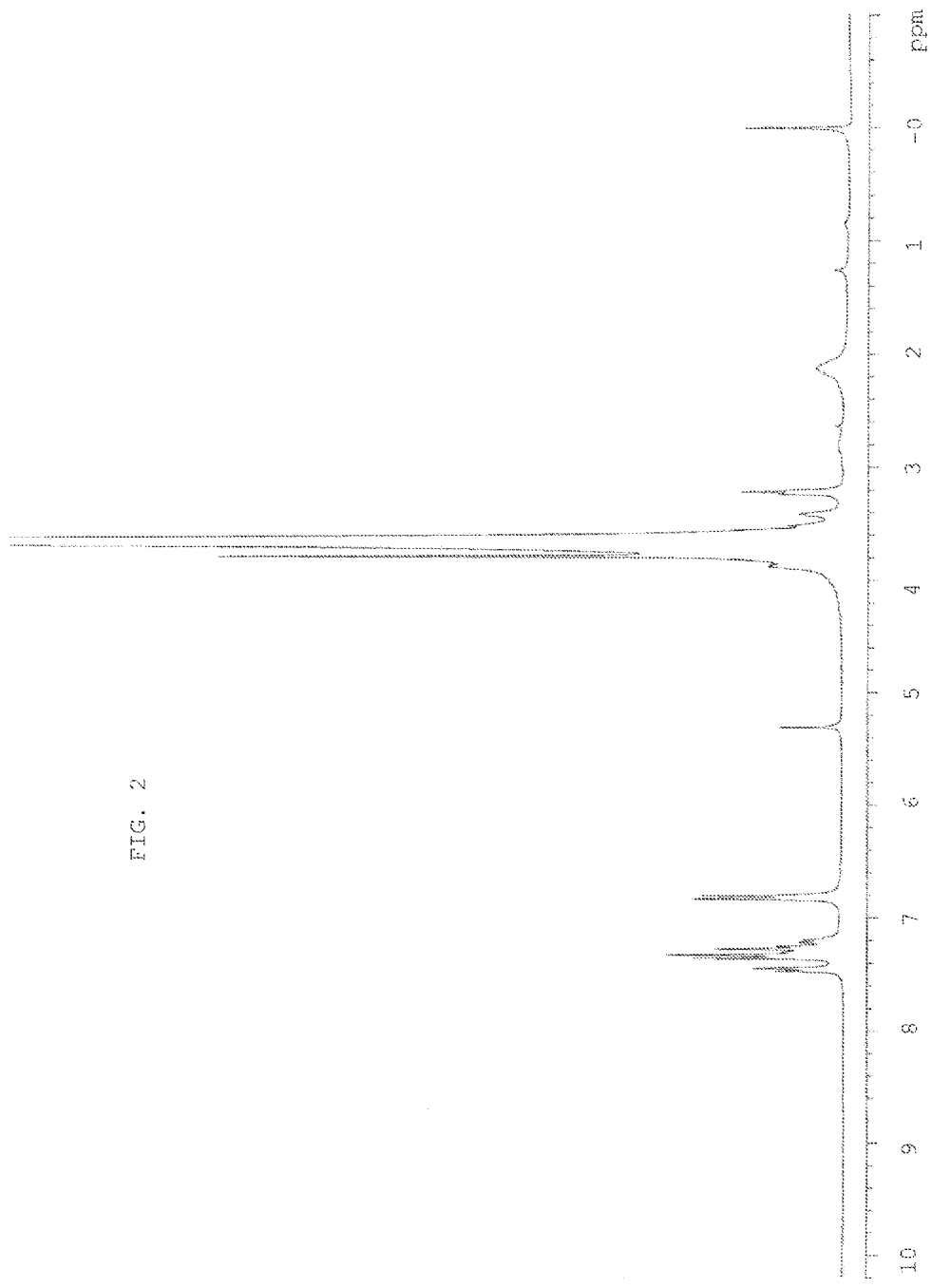
FIG. 2 shows $^1$H NMR data of the compound obtained in Example 1.

$^1$H NMR data of the compound are shown in FIG. 2.

$^1$H NMR (CDCl$_3$); δ 1.93 (br, 1, OH), 3.20-3.80 (m, 186, PEG, DMT-OCH$_3$), 6.80-6.83 (m, 4, DMT), 7.19-7.47 (m, 9, DMT)

Example 1-1-2

Preparation of succinic acid 2-[bis-(4-dimethoxytrityl)-poly(ethyleneglycol)] [Compound A]

3.9 g (1.672 mmol) of 2-[bis-(4-dimethoxytrityl)-poly(ethyleneglycol)] obtained in the example 1-1-1 was dissolved in 20 ml of pyridine, and then cooled to 0° C. 351 mg (3.512 mmol) of succinic acid anhydride (Acros Organics, USA) and 42.5 mg (0.334 mmol) of DMAP (4-dimethylaminopyridine, Sigma Aldrich, USA) were added to the reactant substance, and stirred at 50° C. for 3 days, and then the reaction was finished. The reactant mixture after completion of reaction was vacuum-evaporated to obtain succinic acid 2-[bis-(4-dimethoxytrityl)-poly(ethylene glycol)] [Compound A] 3.65 g (90%, white solid).

Figure 3:
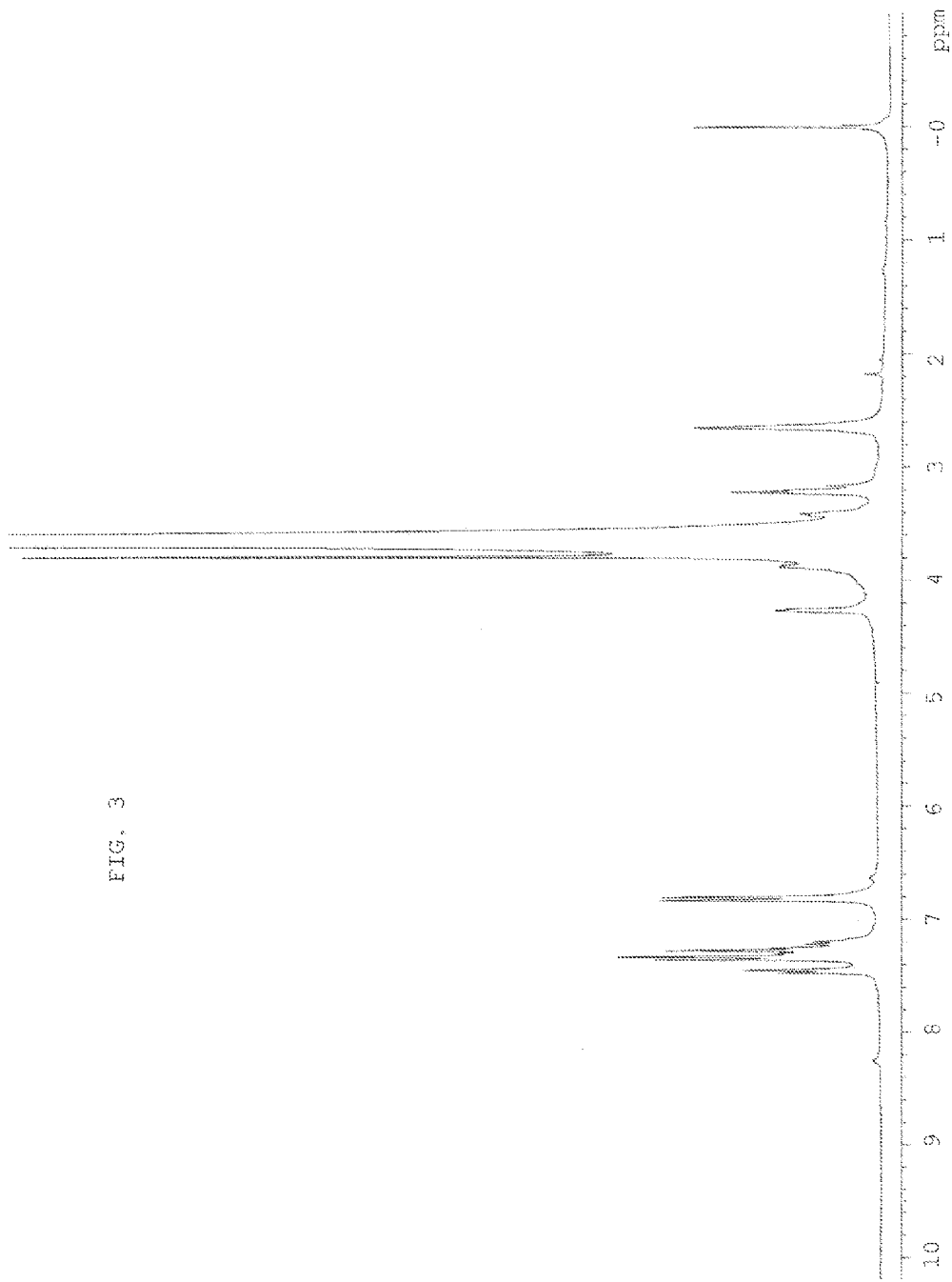
FIG. 3 shows $^1$H NMR data of [Compound A], which is a 3'-PEG reagent for binding with LCAA-CPG in Example 1.

$^1$H NMR data of the compound are shown in FIG. 3.

$^1$H NMR (CDCl$_3$); δ 2.65 (m, 2, CH$_2$CO), 3.20-3.88 (m, 186, PEG, DMT-OCH$_3$), 4.25 (m, 2, CH$_2$CO), 6.80-6.82 (m, 4, DMT), 7.19-7.47 (m, 9, DMT).

Example 1-1-3

Preparation of para-nitrophenyl succinic acid 2-[bis-(dimethoxytrityl)-poly(ethylene glycol))] [Compound B]

1 g (0.411 mmol) of the compound A obtained in the example 1-1-2 was dissolved in 20 ml of methylene chloride (DaeYeon Chemicals, Co. Ltd., Korea), and cooled to 0° C. 143 μl (1.03 mmol) of triethylamine was put into the reactant substance, and 149 mg (0.740 mmol) of 4-nitro phenyl chloroformate was added thereto. Then, the temperature was raised to room temperature and the resultant substance was stirred for 4 hours, and then the reaction was finished. The reactant mixture after completion of reaction was once washed with 20 ml of aqueous saturated NaHCO$_3$ and 20 ml of 1M citric acid (Sigma Aldrich, USA) which was cooled to 0° C.~4° C., and then dried with Na$_2$SO$_4$ (Samchum Chemical Co., Korea). The resultant substance was filtered by using a filtering flask, a Buchner funnel, or an aspirator, followed by vacuum evaporation, to obtain para-nitrophenylsuccinic acid 2-[bis-(4-dimethoxytrityl)-poly(ethylene glycol)[Compound B] 1.0 g (94%, creamy solid).

Figure 4:
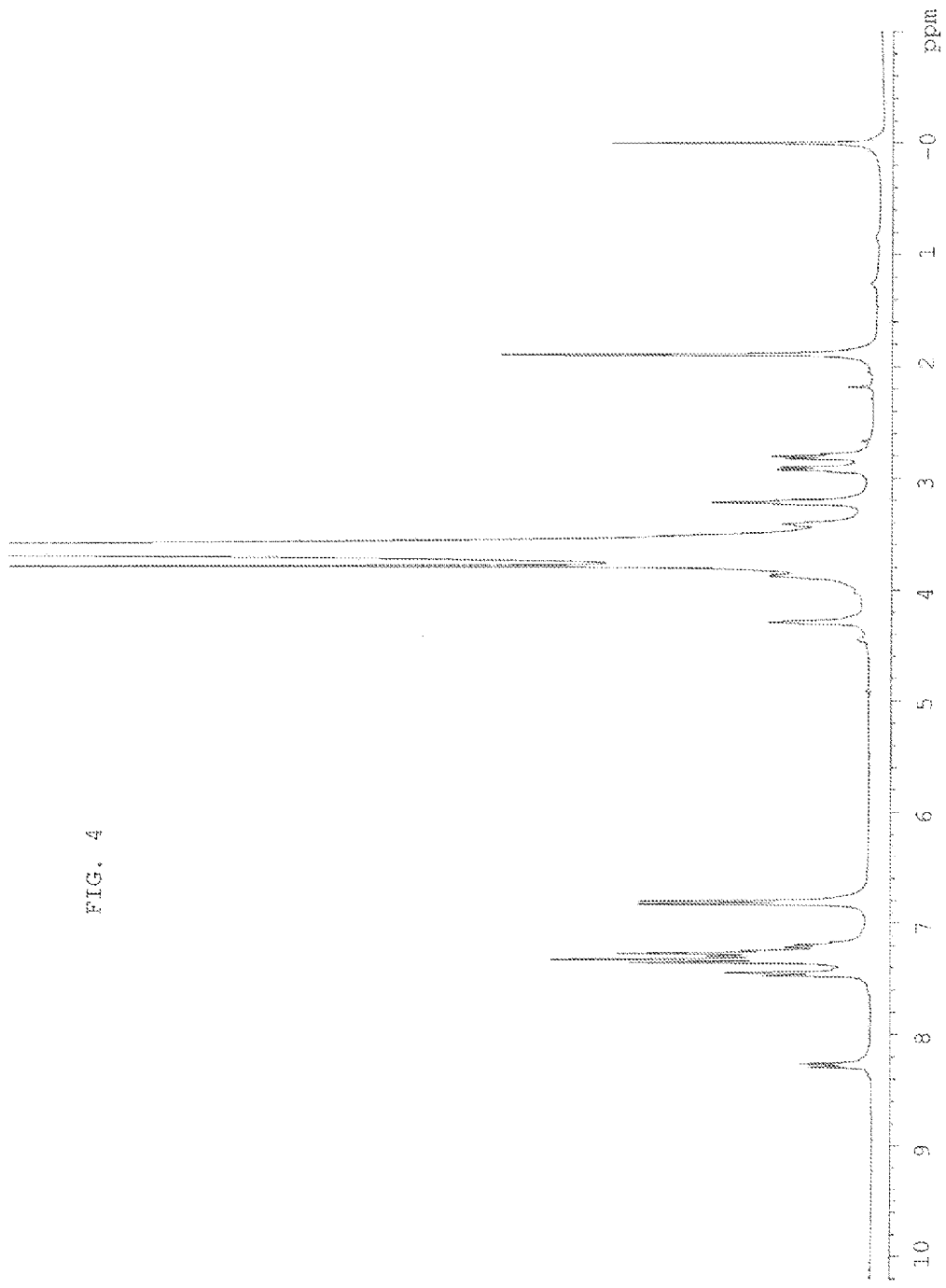
FIG. 4 shows $^1$H NMR data of [Compound B], which is a 3'-PEG reagent for binding with LCAA-CPG in Example 1.

$^1$H NMR data of the compound are shown in FIG. 4.

$^1$H NMR (CDCl$_3$); δ 2.80-2.90 (m, 2, CH$_2$CO), 3.20-3.87 (m, 186, PEG, DMT-OCH$_3$), 4.25 (m, 2, CH$_2$CO), 6.80-6.82 (m, 4, DMT), 7.19-7.47 (m, 9, DMT)

Example 1-1-4

Preparation of 2,5-dioxo-pyrrolidine-1-ylester succinic acid 2-[bis-(4-dimethoxytrityl)-poly(ethylene glycol)] [Compound C]

500 mg (0.206 mmol) of the compound A obtained in the example 1-1-2 was dissolved in 10 ml of methylene chloride, and then 83.14 μl (1.03 mmol) of pyridine was put thereinto. 165 mg (0.781 mmol) of N-succinimidyl trifluoro acetic acid (Sigma Aldrich, USA) was added thereto, and stirred at room temperature for 7 hours, and then the reaction was finished. The reactant mixture after completion of reaction was vacuum evaporated, to obtain 2,5-dioxo-pyrrolidin-1-yl ester succinic acid 2-[bis-(4-dimethoxytrityl)-poly(ethyleneglycol)] [Compound C] 490 mg (94%, white solid).

Figure 5:
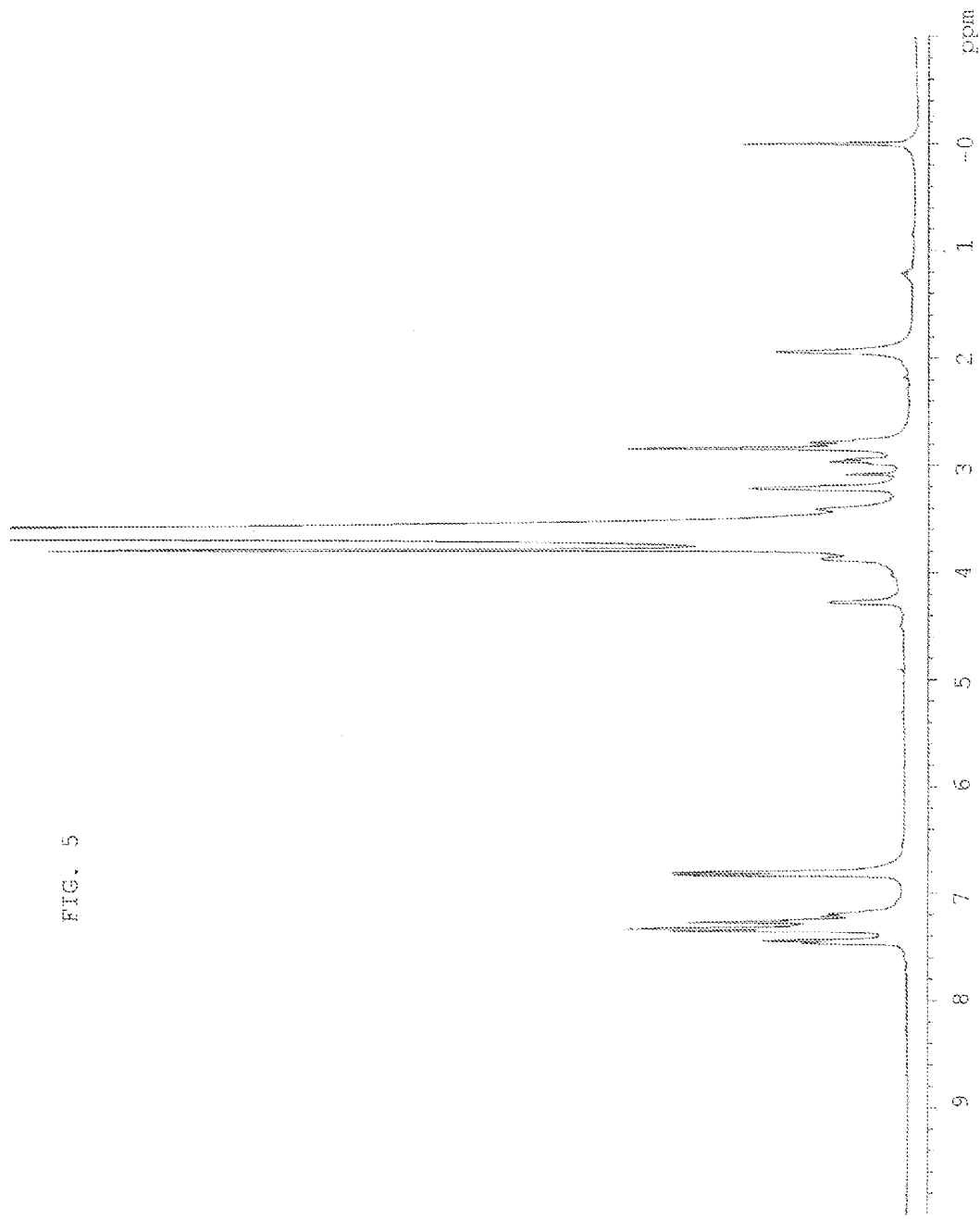
FIG. 5 shows $^1$H NMR data of [Compound C], which is a 3'-PEG reagent for binding with LCAA-CPG in Example.

$^1$H NMR data of the compound are shown in FIG. 5.

$^1$H NMR (CDCl$_3$); δ 2.72-2.97 (m, 6, CH$_2$CO, CH$_2$CH$_2$), 3.20-3.87 (m, 186, PEG, DMT-OCH$_3$), 4.27-4.28 (m, 2, CH$_2$CO), 6.80-6.83 (m, 4, DMT), 7.20-7.47 (m, 9, DMT)

Example 1-2

Binding of LCAA-CPG and 3'-PEG Reagent (Compound A)

In the subsequent example, CPG and 3'-PEG reagent were bound as shown in the following reaction formula:

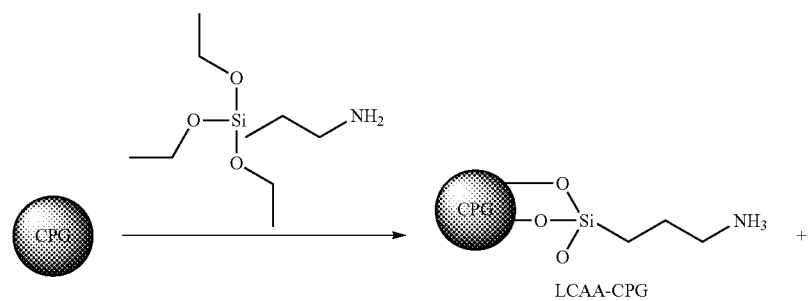

LCAA-CPG

-continued

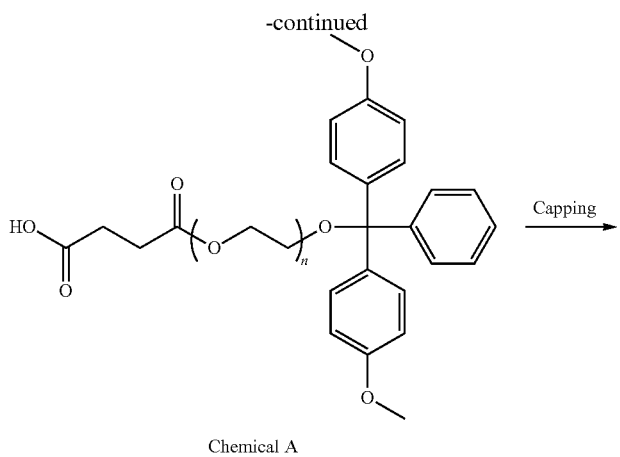

Chemical A

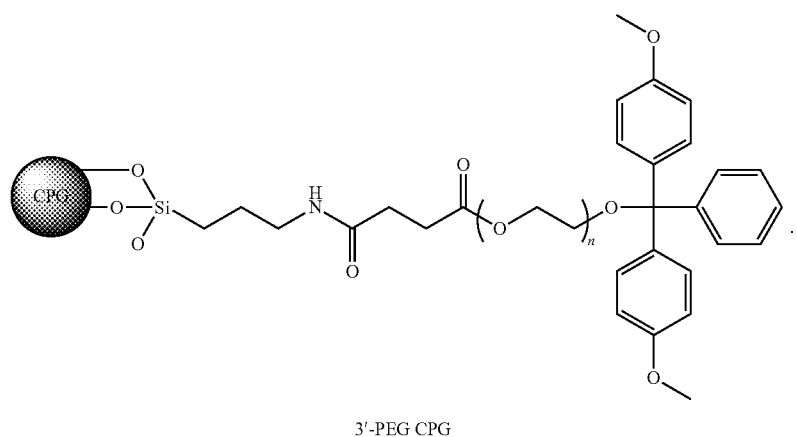

3'-PEG CPG

Example 1-2-1

Preparation of LCAA-CPG (2000 Å)

10 g of CPG (Silicycle Inc., Canada) having a diameter of 40~75 μm and a nanopore of 2000 Å was equally mixed and wet with 100 μm of toluene, and then 2 ml of 3-aminopropyltriethoxysilane (TCI Org. Chem, Japan) was put thereinto. Then, the resultant substance was mixed and then reacted at room temperature for 8 hours. The mixture after completion of reaction was filtered, and washed with methanol, water, and methylene chloride in that order, followed by vacuum drying, to obtain 10 g of LCAA-CPG (2000 Å).

Example 1-2-2

Preparation of 3'-PEG-CPG (2000 Å) using succinic acid 2-[bis-(4 dimethoxytrityl)-poly(ethylene glycol)] [Compound A]

2 g of LCAA-CPG (2000 Å) obtained in the example 1-2-1 was wet in 20 ml of methylene chloride. In addition, the LCAA-CPG (2000 Å) solution was equally mixed with a solution in which 80 mg of the compound A, 14 μl of TEA (triethylamine, Sigma Aldrich, USA). 15 mg of BOP (benzortiazol-1-yloxytris(dimethylamino)phosphonium hexafluorophosphate, TCI Org. Chem, Japan), and 5 mg of HOBT (1-Hydroxybenzotriazole anhydrous, TCI Org. Chem, Japan) were dissolved in 2 ml of methylene chloride. The resultant substance was reacted at reflux for 8 hours, and then the mixture after completion of reaction was filtered and washed with methanol, water, and methylene glycol in that order, followed by vacuum drying.

1 g of the resultant substance was wet in 10 ml of pyridine, and then 1 ml of 1-methylimidazole (Sigma Aldrich, USA) and 1.6 ml of acetic anhydride (Sigma Aldrich, USA) were put thereinto. The resultant substance was equally mixed, and reacted at room temperature for 8 hours. The capping-completed CPG obtained after completion of reaction was washed with methanol, water, methanol, and methylene chloride in that order, followed by vacuum drying, to obtain 1 g of 3'-PEG-CPG.

Example 1-3

Binding of LCAA-CPG (2000 Å) and 3'-PEG Reagent (Compound B)

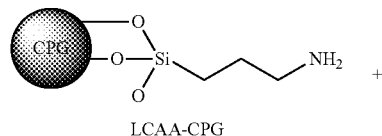

LCAA-CPG

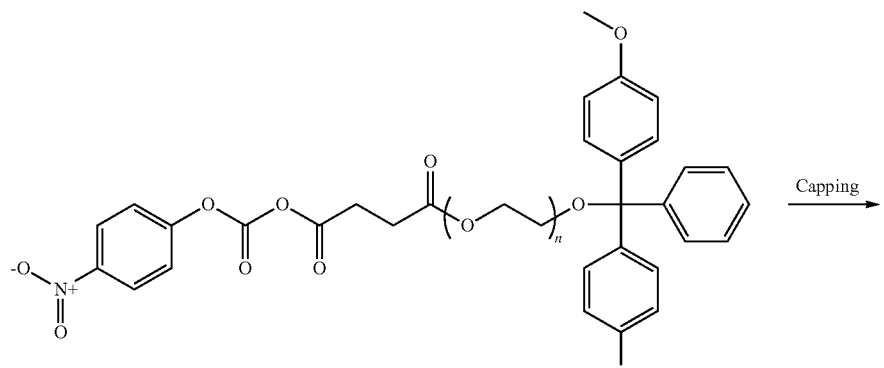

Chemical B

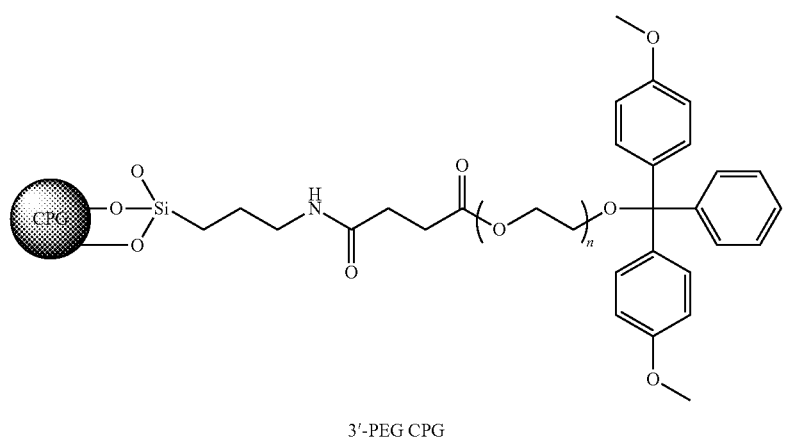

3'-PEG CPG

Preparation of 3'PEG-CPG (2000 Å) was performed by using the compound B.

Specifically, 1 g of LCAA-CPG (2000 Å) obtained in the example 1-2-1 was sufficiently wet in 8 ml of pyridine. In addition, a solution in which 205 mg (2 eq) of the compound B and 55 µl of triethylamine were dissolved in 2 ml of pyridine was equally mixed with the LCAA-CPG solution. The resultant substance was reacted at 50~60° C. for 8 hours, and then the mixture after completion of reaction was filtered. The filtered coupling-CPG was washed with methanol, water, and methylene chloride in that order, followed by vacuum drying. 1 g of the coupling-CPG after completion of drying was wet in 10 ml of pyridine, and then 500 µl of 1-methyl imidazole and 800 µl of acetic anhydride were added thereto. The resultant substance was equally mixed, and then reacted at room temperature for 8 hours. The mixture after completion of reaction was filtered, and then the coupling-CPG was washed with methanol, water, and methylene chloride in that order, followed by vacuum drying, to obtain 3'-PEG-CPG 1 g.

FIG. 6 shows Maldi-T of molecular weight determination results of siRNAs prepared by using 3'-PEG-CPG as a starting material, as shown in the example 2 to be described later.

3'-PEG-CPG preparation sequence;

```
sense
                                      (Sequence ID No. 1)
5'-AAGGAGAUCAACAUUUUCA(dTdT)-PEG(6664.96 Da +
2000 Da)

antisense
                                      (Sequence ID No. 5)
5'-UGAAAAUGUUGAUCUCCUU(dTdT)-PEG(6592.84 Da +
2000 Da)
```

It could be found that Maldi-T of molecular weight has increased by the molecular weight (2000 Da) of PEG.

Example 1-4

Binding of LCAA-CPG (2000 Å) and 3'-PEG Reagent (Compound C)

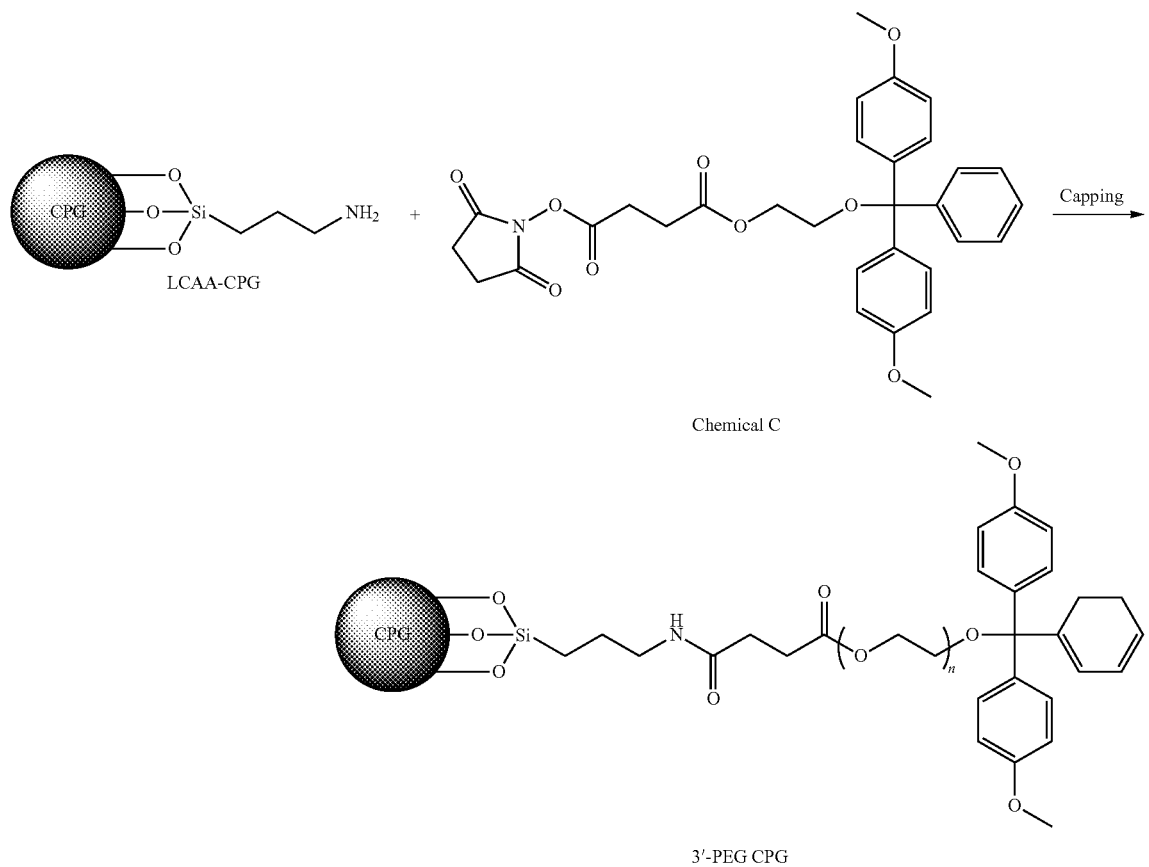

Chemical C

3'-PEG CPG

Preparation of 3'PEG-CPG (2000 Å) was performed by using the compound C.

Specifically, 1 g of LCAA-CPG (2000 Å) obtained in the example 1-2-1 was sufficiently wet in 8 ml of pyridine. In addition, a solution in which 200 mg of the compound C and 55 μl of triethylamine were dissolved in 2 ml of pyridine was equally mixed with the LCAA-CPG solution. The resultant substance was reacted at 50~60° C. for 8 hours, and then the mixture after completion of reaction was filtered. The filtered coupling-CPG was washed with methanol, water, and methylene chloride in that order, followed by vacuum drying. 1 g of the coupling-CPG after completion of drying was wet in 10 ml of pyridine, and then 500 μl of 1-methyl imidazole and 800 μl of acetic anhydride were added thereto. The resultant substance was equally mixed, and then reacted at room temperature for 8 hours. The capping-completed CPG after completion of reaction was washed with methanol, water, and methylene chloride in that order, followed by vacuum drying, to obtain 3'-PEG-CPG 1 g.

FIG. 7 shows results of siRNAs prepared by using 3'-PEG-CPG as a starting material, as shown in the example 2 to be described later.

3'-PEG-CPG preparation sequence;

```
sense
                                    (Sequence ID No. 1)
5'-AAGGAGAUCAACAUUUUCA(dTdT)-PEG(6664.96 Da +
2000 Da)
```

-continued
```
antisense
                                    (Sequence ID No. 5)
5'-UGAAAAUGUUGAUCUCCUU(dTdT)-PEG(6592.84 Da +
2000 Da)
```

It could be found that Maldi-T of molecular weight has increased by the molecular weight (2000 Da) of PEG.

Example 2

Preparation of siRNA-Polymer Compound Conjugates

In the following examples, survivin siRNA was used in order to suppress survivin. The survivin is a protein expressed commonly in most neoplastic tumors or transformed cell lines, tested until now, and thus it is expected to become an important target in anticancer treatment (Abbrosini G. et al. Nat. Med. 3(8): 917-921, 1997). A survivin siRNA sequence of the present invention, when composed of 19 nucleotides, consists of a sense strand of the Sequence ID No. 1 and an antisense strand having a sequence complementary to the sense strand, and beside this, when composed of 23, 27, or 31 nucleotides, has a base sequence of the Sequence ID No. 2, 3, or 4.

(Ssequence ID No. 1.)
5'-AAGGAGAUCAACAUUUUCA-3'

(Ssequence ID No. 2)
5'-AGGAAAGGAGAUCAACAUUUUCA-3'

(Sequence ID No. 3)
5'-AGGAAAGGAGAUCAACAUUUUCAAAUU-3'

(Sequence ID No. 4)
5'-AAAGGAGAUCAACAUUUUCAAAUUAGAUGUU-3'

The siRNA was prepared by linking phosphordiester bonds building an RNA backbone structure, using 13-cyanoethyl phosphoramidite (Shina et al. Nucleic Acids Research, 12:4539-4557, 1984). Specifically, a series of procedures consisting of deblocking, coupling, oxidation and capping were repeatedly performed on a sold support on which nucleotide was attached, by using an RNA synthesizer (384 Synthesizer, BIONEER, Korea), to obtain the reactant containing a desired length of RNA.

Additively, the siRNA-polymer compound conjugate was prepared by linking PEG to a 5'-end region, or hexadecane (C16) or octadecane (C18) saturated hydrocarbon, to the 5'-end region by using a dodecane linker, which is a hydrophobic polymer compound. In addition, the above-mentioned reaction was performed by using 3'PEG-CPG prepared in the example 1 as a support, to obtain the siRNA-polymer compound conjugate in which PEG was provided to 3'-end region.

It was identified whether the reactant substances were consistent with a nucleotide sequence which is to be prepared, by separating RNA from the reactant substances using an HPLC (LC-20A Prominence, SHIMADZU, Japan) and measuring the molecular weight thereof using an MALDI-TOF mass spectrometer (MALDI TOF-MS, SHIMADZU, Japan). After that, a sense RNA strand and an antisense RNA strand were mixed in the same amount, and put into a 1× annealing buffer (30 mM HEPES, 100 Mm potassium acetate, 2 mM magnesium acetate, pH 7.0~7.5). The resultant substance was reacted in a constant temperature bath of 90° C. for 3 minutes, and then again reacted at 37° C., to prepare a double-stranded siRNA-polymer compound conjugate. The prepared siRNA-polymer compound conjugates have structures shown in Table 1. Annealing of the prepared siRNA-polymer compound conjugates was confirmed through electrophoresis photographs (FIG. 8).

TABLE 1

Structures and end modification types of siRNA-polymer compound conjugates

| Conjugate names | Structure names of conjugates | End modification types |
|---|---|---|
| siRNA | naked siRNA | Sense: none<br>Antisense: none |
| siRNA-polymer compound conjugate 1 | 5'PEG-sense siRNA | Sense: 5'PEG<br>Antisense: none |
| siRNA-polymer compound conjugate 2 | 5'PEG-antisense siRNA | Sense: none<br>Antisense: 5'PEG |
| siRNA-polymer compound conjugate 3 | 5'ssPEG-antisense siRNA | Sense: none<br>Antisense: 5'ssPEG |
| siRNA-polymer compound conjugate 4 | 5'PEG + PEG siRNA | Sense: 5'PEG<br>Antisense: 5'PEG |
| siRNA-polymer compound conjugate 5 | 5'PEG + ssPEG siRNA | Sense: 5'PEG<br>Antisense: 5'ssPEG |

TABLE 1-continued

Structures and end modification types of siRNA-polymer compound conjugates

| Conjugate names | Structure names of conjugates | End modification types |
|---|---|---|
| siRNA-polymer compound conjugate 6 | 3'PEG-sense siRNA | Sense: 3'PEG<br>Antisense: none |
| siRNA-polymer compound conjugate 7 | 3'PEG-antisense siRNA | Sense: none<br>Antisense: 3'PEG |
| siRNA-polymer compound conjugate 8 | 3'PEG + PEG siRNA | Sense: 3'PEG<br>Antisense: 3'PEG |
| siRNA-polymer compound conjugate 9 | 5'C18-sense siRNA | Sense: 5'C18-C6-ss-C6<br>Antisense: none |
| siRNA-polymer compound conjugate 10 | 5'C18 + PEG siRNA | Sense: 5'C18-C6-ss-C6<br>Antisense: 5'PEG |
| siRNA-polymer compound conjugate 11 | 5'C16 + PEG siRNA | Sense: 5'C16-C6-ss-C6<br>Antisense: 5'PEG |
| siRNA-polymer compound conjugate 12 | 5'C18-antisense siRNA | Sense: none<br>Antisense: 5'C18-C6-ss-C6 |
| siRNA-polymer compound conjugate 13 | 5'PEG + C18 siRNA | Sense: 5'PEG<br>Antisense: 5'C18-C6-ss-C6 |
| siRNA-polymer compound conjugate 14 | 5'PEG + C16 siRNA | Sense: 5'PEG<br>Antisense: 5'C16-C6-ss-C6 |

*In the structures of conjugates, "ss" means a disulfide bond, and "C16" or "C18" represents C16 or C18 hydrocarbon. Therefore, "C18-C6-ss-C6" and "C16-C6-ss-C6" mean hydrophobic polymer compounds.

Example 3

Evaluation on Stability of siRNA-Polymer Compound Conjugates In Vivo Conditions

It was identified whether or not the siRNA-polymer compound conjugates prepared and separated in the Example 2 have improved stability compared with a naked siRNA in which none of polymer compound is bound. The naked siRNA without modification and the siRNA-polymer compound conjugates 1 to 5 prepared in the Example 2 were incubated for 0, 1, 3, 6, 9, 12, 24, 36, or 48 hours, in a culture medium containing 10% fetal bovine serum (FBS), which imitates in vivo conditions, and then the degrees to which the siRNA was degraded were evaluated by using electrophoresis.

Figure 9:
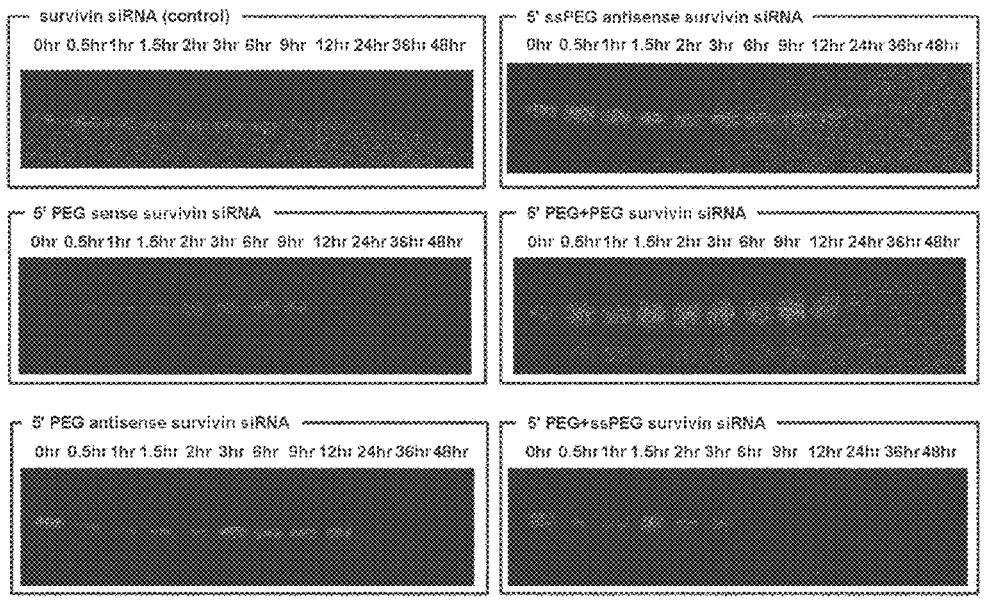
FIG. 9 shows an electrophoresis photograph expressing the degrees of siRNA degradation according to the time in the presence of serum protein, in order to evaluate the stability in the blood of a naked siRNA in which none of polymer compounds are conjugated, and siRNA-polymer compound conjugates in which a hydrophilic polymer compound, PEG is conjugated.

The results showed that siRNA-polymer compound conjugates having PEG introduced therein exhibited siRNA stability for up to 48 hours (FIG. 9). The siRNA stability was exhibited for 12 hours to 24 hours even under the condition of 100% serum.

Example 4

Figure 10:
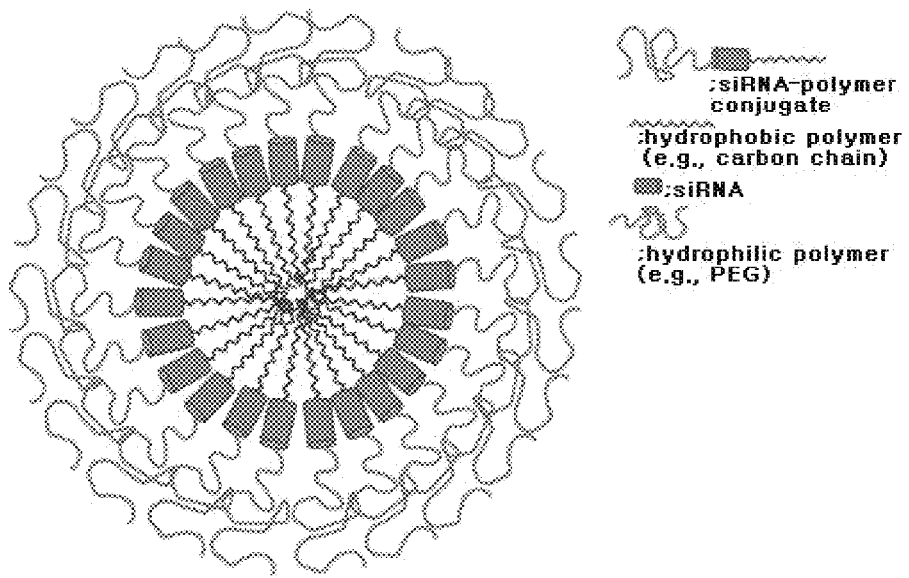
FIG. 10 is a schematic diagram of a nanoparticle formed by a siRNA-polymer compound conjugate.

Measurement on Sizes of Nanoparticles of siRNA-Hydrophobic Polymer Compound Conjugates In each case of siRNA-polymer compound conjugates 9 to 14, a nanoparticle consisting of siRNA-polymer compound conjugates, that is to say, a micelle is formed by hydrophobic interaction between hydrophobic polymer compounds provided at ends of the siRNAs (FIG. 10). The sizes of the nanoparticles were measured using a zeta-potential measuring instrument. The sizes of nanoparticles consisting of the respective siRNA-polymer compound conjugates 9 to 13 prepared in the Example 2, and siRNAs were measured.

Specifically, 2 nmol of siRNA and the siRNA-polymer compound conjugates were dissolved in 1 ml of distilled water, and then the nanoparticles thereof was homogenized (200 W, 40 kHz, 5 sec) by using an ultrasonic homogenizer (Wiseclean, DAIHAN, Korean). The sizes of the homogenized nanoparticles were measured by using the zeta-potential measuring instrument (Nano-ZS, MALVERN, UK). Here, the refractive index and absorption index for materials were set to 1.454 and 0.001, respectively, and the temperature of water as a solvent, 25° C., was input, and the viscosity and refractive index thereof were input. A one-time measurement consists of 20 repetitive size measurements, and this measurement was performed three times.

Figure 11:
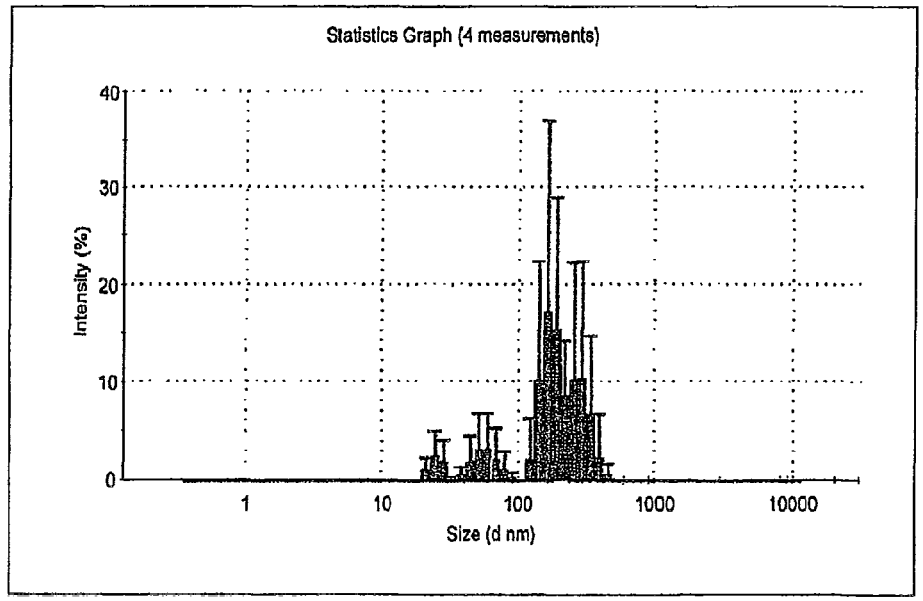
FIG. 11 shows particle size results of nanoparticles consisting of naked siRNAs in which none polymer compounds are conjugated, measured by the zeta-potential measuring instrument.

FIG. 11 shows size results of naked siRNA nanoparticles, measured by the zeta-potential measuring instrument. It showed that sizes of 142-295 nm (maximum point: 164 nm) account for 73.5% of total nanoparticles each consisting of siRNAs.

Figure 12:
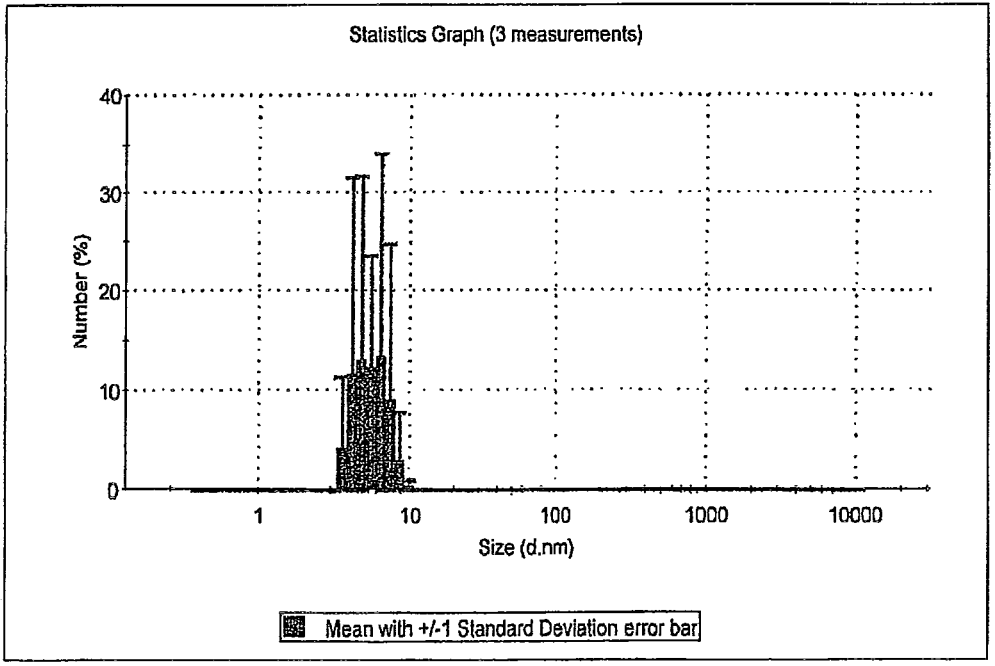
FIG. 12 shows size results of nanoparticles each consisting of siRNA-polymer compound conjugates 9, measured by the zeta-potential measuring instrument.

FIG. 12 shows size results of nanoparticles each consisting of siRNA-polymer compound conjugate 9, measured by the zeta-potential measuring instrument. It showed that sizes of 4.19~7.53 nm (maximum point: 6.50 nm) account for 59.1% of total nanoparticles each consisting of siRNA-polymer compound conjugate 9.

Figure 13:
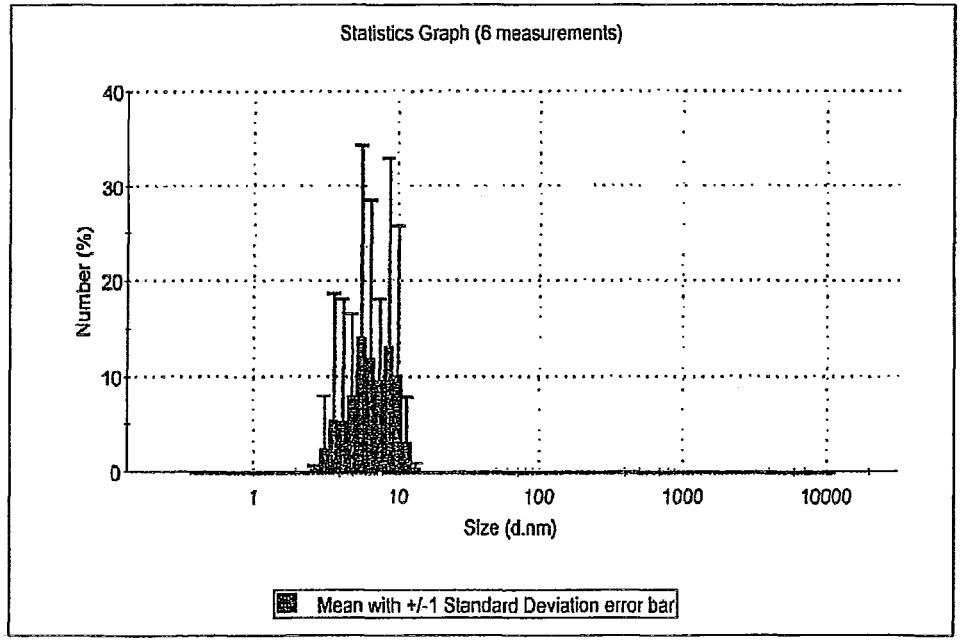
FIG. 13 shows size results of nanoparticles each consisting of siRNA-polymer compound conjugates 10, measured by the zeta-potential measuring instrument.

FIG. 13 shows size results of nanoparticles each consisting of siRNA-polymer compound conjugate 10, measured by the zeta-potential measuring instrument. It showed that sizes of 5.61~10.1 nm (maximum point: 8.72 nm) account for 58.9% of total nanoparticles each consisting of siRNA-polymer compound conjugate 10.

Figure 14:
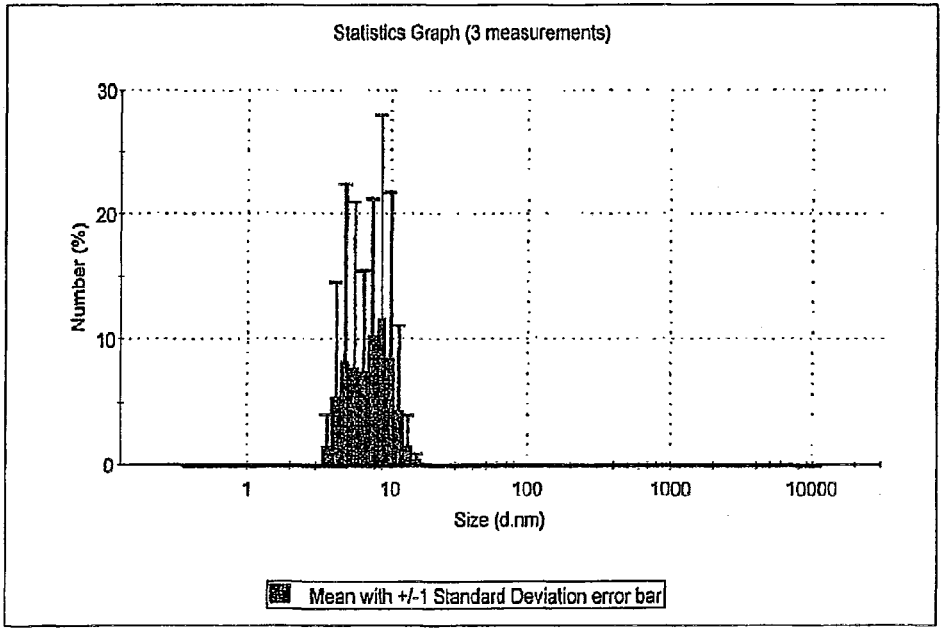
FIG. 14 shows size results of nanoparticles each consisting of siRNA-polymer compound conjugates 11, measured by the zeta-potential measuring instrument.

FIG. 14 shows size results of nanoparticles each consisting of siRNA-polymer compound conjugate 11, measured by the zeta-potential measuring instrument. It showed that sizes of 5.61~10.1 nm (maximum point: 8.72 nm) account for 45.6% of total nanoparticles each consisting of siRNA-polymer compound conjugate 11.

Figure 15:
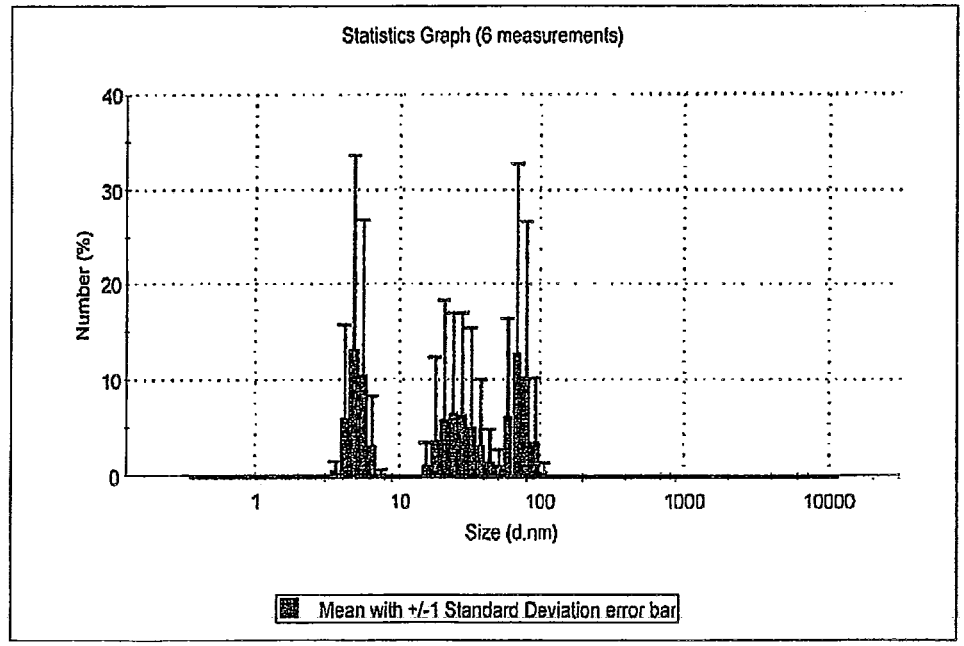
FIG. 15 shows size results of nanoparticles each consisting of siRNA-polymer compound conjugates 12, measured by the zeta-potential measuring instrument.

FIG. 15 shows size results of nanoparticles each consisting of siRNA-polymer compound conjugate 12, measured by the zeta-potential measuring instrument. It showed that sizes of 4.85~5.61 nm account for 23.6%, sizes of 21.0~32.7 nm accounts for 23.5%, and sizes of 68.1~78.8 nm accounts for 23.1% of total nanoparticles each consisting of siRNA-polymer compound conjugate 12.

Figure 16:
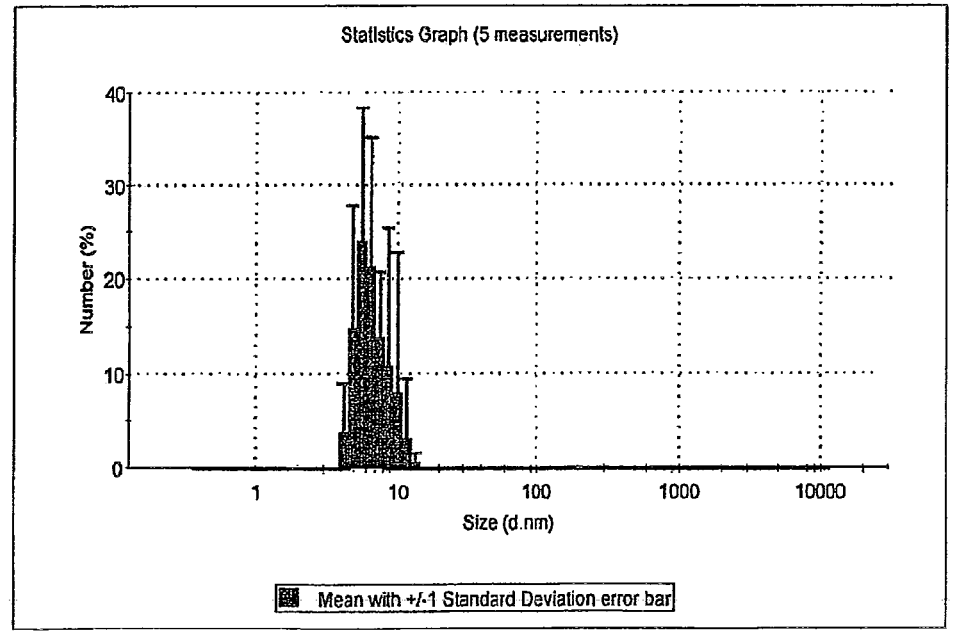
FIG. 16 shows size results of nanoparticles each consisting of siRNA-polymer compound conjugates 13, measured by the zeta-potential measuring instrument.

FIG. 16 shows size results of nanoparticles each consisting of siRNA-polymer compound conjugate 13, measured by the zeta-potential measuring instrument. It showed that sizes of 4.85~8.72 nm (the maximum point: 5.61 nm) account for 84.6% of total nanoparticles each consisting of siRNA-polymer compound conjugate 13.

In cases of siRNA-polymer compound conjugates 9 to 13 except for the siRNA-polymer compound conjugate 12, the sizes of the nanoparticles were mostly 4~8 nm. In the case of the siRNA-polymer compound conjugate 12, the sizes of nanoparticles were variously measured, the reason of which is considered that respective nanoparticles aggregated as time passes during the measuring process, even though homogenization is performed using the ultrasonic homogenizer. As shown in FIGS. 12 to 16, the measured sizes of nanoparticles each consisting of siRNA conjugates exhibit 100 nm or less, which are sufficient sizes to be endocytosed into cells through pinocytosis (Kenneth A. Dawson et al. nature nanotechnology 4:84-85, 2009).

Example 5

Inhibition of Expression of Target Genes in Tumor Cell Lines by Using siRNA-Polymer Compound Conjugates with Transfection Reagents Human cervical cancer cell lines, which are tumor cell lines, were respectively transfected with siRNA-polymer compound conjugates 1 to 8 prepared in the Example 2, and expression levels of survivin gene in the transfected tumor cell lines were analyzed.

Example 5-1

Culture of Tumor Cell Lines

Human cervical cancer cells (HeLa), obtained from American Type Culture Collection (ATCC), were cultured in an RPMI 1640 culture medium (GIBCO, Invitrogen, USA), in which 10% (v/v) fetal bovine serum, penicillin 100 units/ml, and streptomycin 100 μg/ml were added at 37° C. under the condition of 5% (v/v) $CO_2$.

Example 5-2

Inhibition of Expression of Target Gene by Using siRNA-Polymer Compound Conjugates HeLa tumor cell lines were transfected with siRNA-polymer compound conjugates 1 to 8 of Sequence ID No. 1, prepared in the Example 2, and expression of survivin genes in the transfected tumor cell lines were analyzed.

Example 5-2-1

Transfection of Tumor Cell Lines by Using siRNA-Polymer Compound Conjugates $1.3 \times 10^5$ tumor cell lines cultured in the Example 5-1 were cultured in the RPMI 1640 medium within a 6-well plate at 37° C. for 18 hours under the condition of 5% (v/v) $CO_2$, followed by removal of the medium, and then 800 μl of the Opti-MEM medium (GIBCO, USA) was dispensed for each well.

Meanwhile, 2 μl of Lipofectamine™ 2000 (Invitrogen, USA) and 198 μl of Opti-MEM medium were mixed, followed by reaction therebetween at room temperature for 5 minutes, and then 0.8 or 4 μl of the respective siRNA-polymer compound conjugates (25 pmole/μl) prepared in the Examples 2 were added thereto (finally treated at 20 or 100 nM). Then, this resultant substance was again reacted at room temperature for 20 minutes, to prepare a solution.

After that, 200 μl of the transfection solution was dispensed to each of the wells in which the Opti-MEM medium had been dispersed, and the tumor cells were cultured for 6 hours, followed by removal of the Opti-MEM medium. 2.5 ml of the RPMI 1640 culture medium is dispensed thereto, and then the tumor cells were cultured at 37° C. under the condition of 5% (v/v) $CO_2$ for 24 hours.

Example 5-2-2

Relative Quantitative Analysis of Survivin Gene mRNA

Total RNA was extracted from the cell line transfected in the example 5-2-1 to prepare cDNA, and then the quantity of the survivin gene mRNA was relatively quantitated through the realtime PCR.

Example 5-2-2-1

Separation of RNA and Preparation of cDNA from the Transfected Cells

Total RNA was extracted from the cell line transfected in the example 5-2-1 by using an RNA extraction kit (AccuPrep Cell total RNA extraction kit, BIONEER, Korea), and cDNA was prepared from the extracted RNA by using an RNA reverse transcriptase (AccuPower CycleScript RT Premix/dT$_{20}$, BIONEER, Korea), as follows.

Specifically, 1 μg of the extracted RNA was put in each of 0.25 ml Eppendorf tubes containing AccuPower CycleScript RT Premix/dT20 (BIONEER, Korea), and the distilled water treated with diethyl pyrocarbonate (DEPC) was added thereto to have a total volume of 20 μl. By using a PCR machine (MyGenie™ 96 Gradient Thermal Block, BIONEER, Korea), two steps of RNA-primer hybridization at 30° C. for 1 minute and synthesis of cDNA at 52° C. for 4 minutes were repeated six times. Then inactivation of enzyme was performed at 95° C. for 5 minutes to finish the amplification reaction.

Example 5-2-2-2

Relative Quantitative Analysis of Survivin Gene mRNA

The relative quantity of the survivin mRNA was quantitated through the realtime PCR by using the cDNA prepared in the example 5-2-2-1 as a template as follows.

That is to say, the cDNA prepared in the example 5-2-2-1 was 1/5-diluted with the distilled water in each well of a 96-well plate, and then 3 μl of the diluted cDNA, 10 μl of 2× GreenStar™ PCR master mix (BIONEER, Korea), 6 μl of distilled water, and 1 μl of survivin qPCR primer (10 pmole/μl each, BIONEER, Korea) were input to prepare a mixture liquid in order to analyze the survivin expression level. On the other hand, by using HMBS (Hydroxymethylbilane synthase), HPRT1 (Hypoxanthine phosphoribosyl-transferase1), UBC (Ubiquitin C), and YWHAZ (Tyrosine 3-monooxygenase/tryptophan 5-monooxygenase activation protein, zeta polypeptide), which are housekeeping genes (hereafter, referred to as "HK genes"), as the reference gene, in order to normalize the mRNA expression level, the cDNA prepared in the example 5-2-2-1 was 1/5-diluted, and then 3 μl of the diluted cDNA, 10 μl of 2× GreenStar™ PCR master mix (BIONEER, Korea), 6 μl of distilled water, and 1 μl of qPCR primer of each HK gene (10 pmole/μl each, BIONEER, Korea) were input to prepare a HK gene realtime PCR mixture liquid in each well of the 96-well plate. The following reaction was performed on the 96-well plate containing the mixture liquid by using an Exicycler™ 96 Real-Time Quantitative Thermal Block (BIONEER, Korea).

Enzyme activation and secondary structure of cDNA were removed by the reaction at 95° C. for 15 minutes. Then, four steps of denaturing at 94° C. for 30 seconds, annealing at 58° C. for 30 seconds, extension at 72° C. for 30 seconds, and SYBR green scan, were repetitively performed 42 times, and then the final extension at 72° C. for 3 minutes was performed. Then, the temperature was kept at 55° C. for 1 minute, and a melting curve of 55° C.~95° C. was analyzed.

Figure 17:
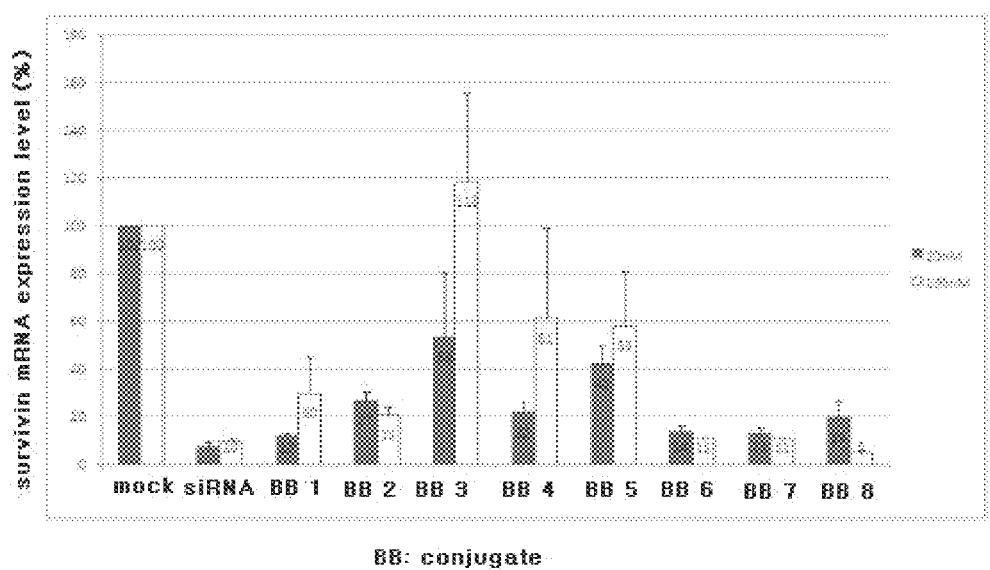
FIG. 17 is a graph comparing mRNA expression degrees of survivin gene after transfection together with a transfection reagent, in order to analyze RNAi effects of a naked siRNA and respective siRNA-polymer compound conjugates in which a hydrophilic polymer compound, PEG, is conjugated.

After finishing the PCR, the survivin Ct (threshold cycle) values obtained respectively were corrected by using the mRNA values (normalization factor, NF) normalized through the HK genes, and then ΔCt values were obtained between the Ct value of a control group treated with only a transfection reagent and the corrected Ct values. The expression rates of survivin mRNA were compared with one another by using the ΔCt values and the calculation equation of $2^{(-\Delta Ct)} \times 100$ (FIG. 17). In FIG. 17, mock means the control group treated with only the transfection reagent.

As a result, as shown in FIG. 17, it showed that RNAi effect of the siRNA was varied depending on end modification types of the siRNA-polymer compound conjugates in which PEG, the hydrophilic polymer compound was conjugated. Particularly, the conjugates 6 to 8 each having the end modification type in which PEG was conjugated to the 3'-end region, exhibited expression-inhibiting degrees similar to that of the naked siRNA. Therefore, the conjugates 6 to 8 are expected to have a little steric hindrance in forming a complex with an RNA-induced silencing complex (RISC) on the RNAi mechanism of the siRNA. In addition, most siRNA-PEG conjugates exhibited higher inhibition of target gene mRNA expression in a low concentration (20 nM) treatment condition than in a high concentration (100 nM) treatment condition, and thus it is expected that siRNA is prevented from being bound with the RISC due to the PEG as the concentration condition of the siRNA-PEG conjugate is higher.

Example 5-3

Inhibition of Expression of Target Gene by Using Long-Sequence siRNA-Polymer Compound Conjugates When the cells were transfected with siRNA-hydrophilic polymer compound conjugates together with a transfection reagent, inhibition of target gene mRNA expression was anaylzed. Here, the siRNAs, in which end modification into the structure of siRNA-polymer compound conjugate 4 was induced for each base sequence of siRNA Sequence ID No. 1 to 4, were used.

Example 5-3-1

Transfection of Tumor Cell Lines by Using siRNA-Polymer Compound Conjugates $1.3 \times 10^5$ tumor cell lines cultured in the Example 5-1 were cultured in the RPMI 1640 medium within a 6-well plate at 37° C. for 24 hours under the condition of 5% (v/v) $CO_2$, followed by removal of the medium, and then 800 μl of the Opti-MEM medium was dispensed for each well.

Meanwhile, 2 μl of Lipofectamine™ 2000 and 198 μl of the Opti-MEM medium were mixed, followed by reaction therebetween at room temperature for 5 minutes, and then 0.8 or 4 μl of the respective siRNA-polymer compound conjugates (25 pmole/μl) prepared in the Examples 2 were added thereto (finally treated at 20 or 100 nM). Then, this resultant substance was again reacted at room temperature for 20 minutes, to prepare a solution.

After that, 200 μl of a transfection solution was dispensed to each of the wells in which the Opti-MEM medium had been dispersed, and the tumor cells were cultured for 6 hours, followed by removal of the Opti-MEM medium. 2.5 ml of the RPMI 1640 culture medium is dispensed thereto, and then the tumor cells were cultured at 37° C. under the condition of 5% (v/v) $CO_2$ for 24 hours.

Example 5-3-2

Relative Quantitative Analysis of Survivin Gene mRNA

Total RNA was extracted from the cell line transfected in the example 5-3-1 to prepare cDNA, and then the quantity of survivin gene mRNA was relatively quantitated through the real-time PCR.

Example 5-3-2-1

Separation of RNA and Preparation of cDNA from the Transfected Cells

Total RNA was extracted from the cell line transfected in the example 5-3-1 by using an RNA extraction kit (AccuPrep Cell total RNA extraction kit, BIONEER, Korea), and cDNA was prepared from the extracted RNA by using an RNA reverse transcriptase (AccuPower CycleScript RT Premix/ dT$_{20}$, BIONEER, Korea), as follows.

Specifically, 1 µg of the extracted RNA was put into each of 0.25 ml Eppendorf tubes containing AccuPower CycleScript RT Premix/dT20 (BIONEER, Korea), and the distilled water treated with diethyl pyrocarbonate (DEPC) was added thereto to have a total volume of 20 µl. By using a PCR machine (MyGenie™ 96 Gradient Thermal Block, BIONEER, Korea), two steps of RNA-primer hybridization at 30° C. for 1 minute and preparation of cDNA at 52° C. for 4 minutes were repeated six times. Then inactivation of enzyme was performed at 95° C. for 5 minutes to finish the amplification reaction.

Example 5-3-2-2

Relative Quantitative Analysis of Survivin Gene mRNA

The relative quantity of the survivin gene mRNA was quantitated through the realtime PCR by using the cDNA prepared in the example 5-3-2-1 as a template as follows.

That is to say, the cDNA prepared in the example 5-3-2-1 was 1/5-diluted in each well of a 96-well plate, and then 3 µl of the diluted cDNA, 10 µl of 2× GreenStar™ PCR master mix (BIONEER, Korea), 6 µl of distilled water, and 1 µl of survivin qPCR primer (10 pmole/µl each, BIONEER, Korea) were input to prepare a mixture liquid in order to analyze the survivin expression level. On the other hand, by using HMBS, HPRT1, UBC, and YWHAZ, which are HK gene, as the reference gene, in order to normalize the mRNA expression level, the cDNA prepared in the example 5-3-2-1 was 1/5-diluted, and then 3 µl of the diluted cDNA, 10 µl of 2× GreenStar™ PCR master mix (BIONEER, Korea), 6 µl of distilled water, and 1 µl of qPCR primer of each HK gene (10 pmole/µl each, BIONEER, Korea) were input to prepare a HK gene realtime PCR mixture liquid in each well of the 96-well plate. The following reaction was performed on the 96-well plate containing the mixture liquid by using an Exicycler™ 96 Real-Time Quantitative Thermal Block (BIONEER, Korea).

Enzyme activation and secondary structure of cDNA were removed by the reaction at 95° C. for 15 minutes. Then, four steps of denaturing at 94° C. for 30 seconds, annealing at 58° C. for 30 seconds, extension at 72° C. for 30 seconds, and SYBR green scan were repetitively performed 42 times, and then the final extension at 72° C. for 3 minutes was performed. Then the temperature was kept at 55° C. for 1 minute, and a melting curve of 55° C.~95° C. was analyzed.

Figure 18:
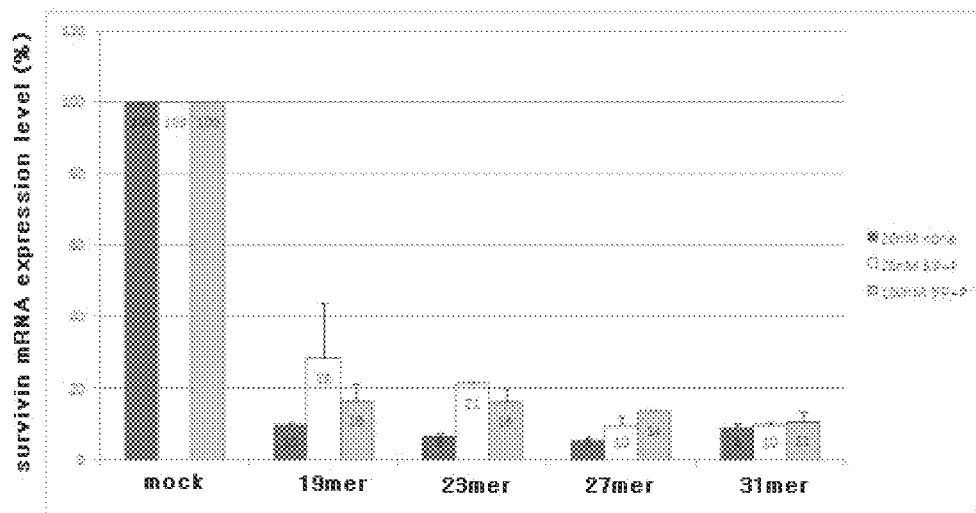
FIG. 18 is a graph comparing mRNA expression degrees of survivin gene after transfection together with a transfection reagent, in order to analyze RNAi effects of a naked siRNA and respective long-sequence siRNAs transformed in the siRNA-polymer compound conjugate 4.

After finishing the PCR, the survivin Ct (threshold cycle) values obtained respectively were corrected by using the mRNA values (normalization factor, NF) normalized through the HK genes, and then ΔCt values were obtained between the Ct value of a control group treated with only the transfection reagent and the corrected Ct values. The expression rates of survivin mRNA were compared with one another by using the ΔCt values and the calculation equation of $2^{(-\Delta Ct)} \times 100$ (FIG. 18). In FIG. 18, mock means the control group treated with only the transfection reagent, and 19mer, 23mer, 27mer, and 31mer represent Sequence ID No. 1 to 4, respectively. 5'P+P represents a structure of the siRNA-polymer compound conjugate 4. The cells were treated with 20 nM and 100 nM respectively, and the inhibition degrees of the target gene expression were compared with one another.

As a result, as shown in FIG. 18, the long-chain naked siRNAs transformed in the form of siRNA-polymer compound conjugate 4, exhibited less difference in inhibition of the target gene mRNA expression, compared with the naked siRNA. Therefore, it could be found that the transformed long-chain siRNA decreases the steric hindrance phenomenon due to PEG compared with a shot chain.

That is to say, in a case of the long-chain siRNA, the siRNA is cleaved in a structure of 19+2 by a dicer in an operation mechanism of RNAi, and the cleaved siRNA is bound to an RISC complex to cause the operation mechanism of RNAi. For this reason, the long-chain siRNA, in which PEG is provided at both end regions, causes existence of a large quantity of siRNAs without PEG attachment, and thus has a relatively high interaction with the RISC complex, compared with the Sequence ID No. 1, which is believed to maintain the RNAi induction effect.

Example 6

Inhibition of Expression of Target Gene in Tumor Cell Lines by Using Only siRNA-Polymer Compound Conjugates without Transfection Reagents HeLa tumor cell lines were transfected with siRNA-polymer compound conjugates 1 to 14 prepared in the Example 2, and expression of survivin genes of the transfected tumor cell lines was analyzed.

Example 6-1

Culture of Tumor Cell Lines

Human uterine cancer cells (HeLa), obtained from American Type Culture Collection (ATCC), were cultured in an RPMI 1640 culture medium (GIBCO/Invitrogen, USA), in which 10% (v/v) fetal bovine serum, penicillin 100 units/ml, and streptomycin 100 µg/ml were added, at 37° C. under the conditions of 5% (v/v) CO$_2$.

Example 6-2

Transfection of Tumor Cell Lines by Using siRNA-Polymer Compound Conjugates $1.3 \times 10^5$ tumor cell lines cultured in the Example 6-1 were cultured in the RPMI 1640 medium in a 6-well plate at 37° C. for 24 hours under the condition of 5% (v/v) CO$_2$, followed by removal of the medium, and then 900 µl of the Opti-MEM medium was dispensed for each well.

Meanwhile, 100 µl of the Opti-MEM medium, 5 or 10 µl of the respective siRNA-polymer compound conjugates 1 to 5 (1 nmole/µl) prepared in the example 2 were added thereto (finally treated at 500 nM or 1 µM), and the resultant substance was again reacted at room temperature for 20 minutes, to prepare the solution.

Meanwhile, 100 µl of the Opti-MEM medium, 5 or 10 µl of the respective siRNA-polymer compound conjugates 9 to 14 (1 nmole/µl) prepared in the example 2 were added thereto (finally treated 500 nM or 1 µM), and micelles consisting of siRNA-hydrophobic polymer compound conjugates were homogenized through sonication by high frequency sounds, to prepare the solution.

After that, 100 μl of the transfection solution was dispensed to each of the wells in which the Opti-MEM medium had been dispersed, and the tumor cells were cultured for 24 hours, followed by addition of 1 ml of RPMI 1640 medium containing 20% FBS. The cells were further cultured at 37° C. for 24 hours under the condition of 5% (v/v) $CO_2$, treated with siRNA-polymer compound conjugates, and then cultured for total 48 hours.

Example 6-3

Relative Quantitative Analysis of Survivin Gene mRNA

Total RNA was extracted from the cell line transfected in the example 6-2 to prepare cDNA, and then the quantity of survivin gene mRNA was relatively quantitated through the real-time PCR.

Example 6-3-1

Separation of RNA and Preparation of cDNA From the Transfected Cells

Total RNA was extracted from the cell line transfected in the example 6-2 by using an RNA extraction kit (AccuPrep Cell total RNA extraction kit, BIONEER, Korea), and cDNA was prepared from the extracted RNA by using an RNA reverse transcriptase (AccuPower CycleScript RT Premix/$dT_{20}$, BIONEER, Korea), as follows.

Specifically, 1 μg of the extracted RNA was put in each of 0.25 ml Eppendorf tubes containing AccuPower CycleScript RT Premix/dT20 (BIONEER, Korea), and the distilled water treated with diethyl pyrocarbonate (DEPC) was added thereto to have a total volume of 20 μl. By using a PCR machine (MyGenie™ 96 Gradient Thermal Block, BIONEER, Korea), two steps of RNA-primer hybridization at 30° C. for 1 minute and preparation of cDNA at 52° C. for 4 minutes were repeated six times. Then inactivation of enzyme was performed at 95° C. for 5 minutes to finish the amplification reaction.

Example 6-3-2

Relative Quantitative Analysis of Survivin Gene mRNA

The relative quantity of survivin gene mRNA was quantitated through the realtime PCR by using the cDNA prepared in the example 6-3-1 as a template as follows.

That is to say, the cDNA prepared in the example 6-3-1 was 1/5-diluted in each well of a 96-well plate, and then 3 μl of the diluted cDNA, 10 μl of 2× GreenStar™ PCR master mix (BIONEER, Korea), 6 μl of distilled water, and 1 μl of survivin qPCR primer (10 pmole/μl each, BIONEER, Korea) were used to prepare a mixture liquid in order to analyze the survivin expression level. On the other hand, by using HMBS (Hydroxymethyl-bilane synthase), HPRT1 (Hypoxanthine phosphoribosyl-transferase1), UBC (Ubiquitin C), YWHAZ (Tyrosine 3-monooxygenase/tryptophan 5-monooxygenase activation protein, zeta polypeptide), which are housekeeping genes (hereafter, referred to as "HK genes"), as the reference gene, in order to normalize the mRNA expression level, the cDNA prepared in the example 6-3-1 was 1/5-diluted, and then 3 μl of the diluted cDNA, 10 μl of 2× GreenStar™ PCR master mix (BIONEER, Korea), 6 μl of distilled water, and 1 μl of qPCR primer of each HK gene (10 pmole/μl each, BIONEER, Korea) were input to prepare a HK gene realtime PCR mixture liquid in each well of the 96-well plate. The following reaction was performed on the 96-well plate containing the mixture liquid by using an Exicycler™ 96 Real-Time Quantitative Thermal Block (BIONEER, Korea).

Enzyme activation and secondary structure of cDNA were removed by the reaction at 95° C. for 15 minutes. Then, four steps of denaturing at 94° C. for 30 seconds, annealing at 58° C. for 30 seconds, extension at 72° C. for 30 seconds, and SYBR green scan were repetitively performed 42 times, and then the final extension at 72° C. for 3 minutes was performed. Then the temperature was kept at 55° C. for 1 minute, and a melting curve of 55° C.~95° C. was analyzed. After finishing the PCR, the survivin Ct (threshold cycle) values obtained respectively were corrected by using the mRNA values (normalization factor, NF) normalized through the HK genes, and then ΔCt value was obtained between the Ct value of a control group treated with only the transfection reagent and the corrected Ct values. The expression rates of survivin mRNA were compared with one another by using the ΔCt values and the calculation equation of $2^{(-\Delta Ct)} \times 100$ (FIG. 19).

Figure 19:
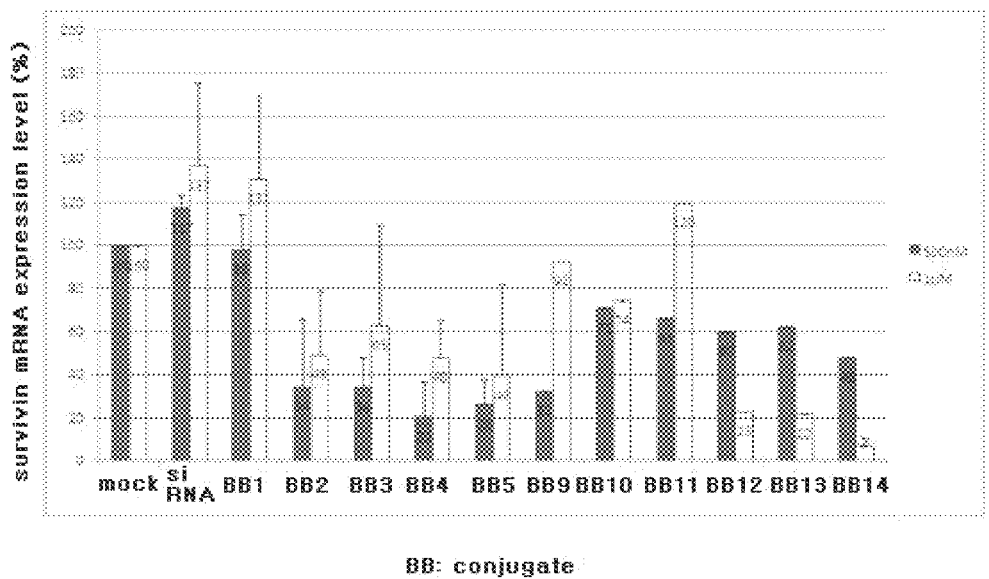
FIG. 19 is a graph comparing mRNA expression degrees of survivin gene after transfection in absence of a transfection reagent, in order to analyze RNAi effects of a naked siRNA and siRNA-polymer compound conjugates 1 to 5 and 9 to 14.

As a result, as shown in FIG. 19, the siRNA PEG conjugates of the conjugates 2 to 5 highly inhibit the survivin mRNA level, compared with the siRNA-polymer compound conjugate 1, unlike the result of the case in which transfection was performed through the transfection reagent. The siRNA-polymer compound conjugates 1 to 5 exhibited higher RNAi effect in a low concentration (500 nM) than in a high concentration. In addition, the siRNA-hydrophobic polymer compound conjugates of the conjugates 9 to 14 exhibited a lower inhibition of the survivin mRNA expression level, compared with the siRNA conjugates 1 to 5, when treated at the same concentration (500 nM). However, when treated at the high concentration condition (1 uM), particularly the end modification of the siRNA-polymer compound conjugate 14 leads to high inhibition effect of the survivin mRNA expression level.

The invention claimed is:

1. A conjugate of survivin-specific siRNA and polymer compound, of the structure below:

A-X—R—Y—B wherein:
one of A and B is a hydrophilic polymer compound and the other thereof is a hydrophobic compound;
X and Y each are independently a simple covalent bond or a linker-mediated covalent bond; and
R is a survivin-specific siRNA,
wherein the hydrophobic compound is $C_{16}$~$C_{50}$ hydrocarbon or cholesterol which has a molecular weight of 250 to 1,000.

2. The conjugate of claim 1, wherein a single strand of the survivin-specific siRNA (R) is composed of 19 to 31 nucleotides.

3. The conjugate of claim 1, wherein the survivin-specific siRNA (R) comprises sense strand having a nucleotide sequence selected from nucleotide sequences of SEQ ID NOs.: 1 to 4 and an antisense strand having a nucleotide sequence complementary to the sequence of the sense strand.

4. The conjugate of claim 1, wherein the survivin-specific siRNA(R) has chemical modification.

5. The conjugate of claim 4, wherein the chemical modification includes at least one modification selected from:
modification of a phosphorodiester bond into a phosphorothioate linkage; modification of —OH at the 2'-position of a pentose into 2'-$OCH_3$ or 2'-dioxy-2'-fluouridine; and
modification of —OH at the 2' position of the pentose into an LNA type formed by linking the 2' position and the 4' position of the pentose.

6. The conjugate of claim 1, wherein:
the hydrophilic polymer compound is a non-ionic polymer compound having a molecular weight of 1,000 to 10,000; and
the simple covalent bond or linker-mediated covalent bond is a non-degradable bond or a degradable bond.

7. The conjugate of claim 6, wherein the non-degradable bond is an amide bond or a phosphate bond; and the degradable bond is selected from a disulfide bond, an acid-cleavable bond, an ester bond, an anhydride bond, a biodegradable bond and an enzyme-cleavable bond.

8. The conjugate of claim 6, wherein the hydrophilic polymer compound includes at least one selected from polyethyleneglycol, polyvinylpyrolidone, and polyoxazoline.

9. A nanoparticle comprising the conjugate of claim 1.

10. A composition comprising the conjugate of claim 1 as a pharmaceutically effective component.

11. A composition comprising the nanoparticle of claim 9 as a pharmaceutically effective component.

* * * * *

UNITED STATES PATENT AND TRADEMARK OFFICE
CERTIFICATE OF CORRECTION

PATENT NO. : 8,772,472 B2
APPLICATION NO. : 13/613071
DATED : July 8, 2014
INVENTOR(S) : Bo Ram Han et al.

Page 1 of 2

It is certified that error appears in the above-identified patent and that said Letters Patent is hereby corrected as shown below:

In the Specification

Column 1, line 20: "Aug. 15, 2012" should be -- Aug. 15, 2012. --.

Column 14, lines 48 and 51: "Maldi-T of" should be -- Maldi-Tof --.

Column 19, lines 8, 9, 14, 15, 31, and 52: "ml" should be -- ml --.

Column 20, lines 2 and 31: "µl" should be -- µl --.

Column 20, lines 8 and 30: "ml" should be -- ml --.

Column 21, lines 53 and 67: "ml" should be -- ml --.

Column 22, line 48: "µl" should be -- µl --.

Column 22, lines 54, 59, 60, and 61: "ml" should be -- ml --.

Column 23, lines 57, 59, and 66: "ml" should be -- ml --.

Column 23, lines 59, 66, and 67: "µl" should be -- µl --.

Column 24, line 54: "Maldi-T of" should be -- Maldi-Tof --.

Column 25, line 1: "Maldi-T of" should be -- Maldi-Tof --.

Column 25, lines 48, 50, and 58: "ml" should be -- ml --.

Column 25, lines 50, 58, and 59: "µl" should be -- µl --.

Column 26, line 51: "Maldi-T of" should be -- Maldi-Tof --.

Column 27, line 16: "13-cyanoethyl" should be -- β-cyanoethyl --.

Column 29, line 2: "ml" should be -- ml --.

Column 30, lines 11 and 46: "ml" should be -- ml --.

Column 30, lines 32, 35, 36, 38, 39, and 43: "µl" should be -- µl --.

Column 31, line 6: "ml" should be -- ml --.

Column 31, lines 27, 28, 29, 39, 40, 41, and 42: "µl" should be -- µl --.

Column 32, lines 43, 46, and 51: "µl" should be -- µl --.

Signed and Sealed this
Twenty-fifth Day of November, 2014

Michelle K. Lee
*Deputy Director of the United States Patent and Trademark Office*

CERTIFICATE OF CORRECTION (continued)
U.S. Pat. No. 8,772,472 B2

Column 32, line 54: "ml" should be -- ml --.

Column 33, line 13: "ml" should be -- ml --.

Column 33, lines 16, 33, 34, 35, 36, 42, 43, and 44: "µl" should be -- µl --.

Column 34, lines 44 and 45: "ml" should be -- ml --.

Column 34, lines 56, 58, 60, 64, and 66: "µl" should be -- µl --.

Column 35, line 7: "ml" should be -- ml --.

Column 35, lines 4 and 38: "µl" should be -- µl --.

Column 36, lines 2, 3, 4, 5, 14, 15, and 16: "µl" should be -- µl --.